US012766183B2

(12) United States Patent
Beier et al.

(10) Patent No.: US 12,766,183 B2
(45) **Date of Patent: *Oct. 20, 2026**

(54) OPHTHALMIC COMPOSITION FOR TREATMENT OF DRY EYE DISEASE

(71) Applicant: NOVALIQ GMBH, Heidelberg (DE)

(72) Inventors: Markus Beier, Weinheim (DE); Jörg Haisser, Siegelsbach (DE); Alice Meides, Heidelberg (DE); Sonja Krösser, Heidelberg (DE); Hartmut Voss, Schriesheim (DE); Frank Löscher, Schriesheim (DE); Bernhard Günther, Dossenheim (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 19/413,977

(22) Filed: Dec. 9, 2025

(65) Prior Publication Data

US 2026/0091084 A1 Apr. 2, 2026

Related U.S. Application Data

(60) Continuation of application No. 17/933,471, filed on Sep. 19, 2022, now Pat. No. 12,496,326, which is a division of application No. 16/109,127, filed on Aug. 22, 2018, now abandoned, which is a continuation of application No. PCT/EP2017/083770, filed on Dec. 20, 2017.

(30) Foreign Application Priority Data

Dec. 23, 2016 (EP) .................................... 16206735
Apr. 7, 2017 (EP) .................................... 17165578

(51) Int. Cl.

| | |
|---|---|
| ***A61K 38/13*** | (2006.01) |
| ***A61J 1/00*** | (2023.01) |
| ***A61K 9/00*** | (2006.01) |
| ***A61K 9/08*** | (2006.01) |
| ***A61K 31/00*** | (2006.01) |
| ***A61K 47/06*** | (2006.01) |
| ***A61K 47/10*** | (2017.01) |
| ***A61P 27/02*** | (2006.01) |

(52) U.S. Cl.

CPC ................ *A61K 38/13* (2013.01); *A61J 1/00* (2013.01); *A61K 9/0048* (2013.01); *A61K 9/08* (2013.01); *A61K 31/00* (2013.01); *A61K 47/06* (2013.01); *A61K 47/10* (2013.01); *A61P 27/02* (2018.01)

(58) Field of Classification Search

None

See application file for complete search history.

(56) References Cited

U.S. PATENT DOCUMENTS

| | | | |
|---|---|---|---|
| 2,616,927 | A | 11/1952 | Kauck et al. |
| 4,452,818 | A | 6/1984 | Haidt |
| 5,077,036 | A | 12/1991 | Long |
| 5,326,566 | A | 7/1994 | Parab |
| 5,336,175 | A | 8/1994 | Mames |
| 5,370,313 | A | 12/1994 | Beard |
| 5,518,731 | A | 5/1996 | Meadows |
| 5,578,020 | A | 11/1996 | Mosley |
| 5,667,809 | A | 9/1997 | Trevino et al. |
| 5,704,906 | A | 1/1998 | Fox |
| 5,874,469 | A | 2/1999 | Maniar et al. |
| 5,874,481 | A | 2/1999 | Weers et al. |
| 5,980,936 | A | 11/1999 | Krafft et al. |
| 5,981,607 | A | 11/1999 | Ding et al. |
| 6,042,845 | A | 3/2000 | Sun et al. |
| 6,060,085 | A | 5/2000 | Osborne |
| 6,113,919 | A | 9/2000 | Reiss et al. |
| 6,159,977 | A | 12/2000 | Reeves |
| 6,177,477 | B1 | 1/2001 | George et al. |
| 6,197,323 | B1 | 3/2001 | Georgieff |
| 6,224,887 | B1 | 5/2001 | Samour et al. |
| 6,294,563 | B1 | 9/2001 | Garst |
| 6,335,335 | B2 | 1/2002 | Higashiyama et al. |
| 6,372,243 | B2 | 4/2002 | Kobuch et al. |
| 6,391,879 | B1 | 5/2002 | Reeves |
| 6,458,376 | B1 | 10/2002 | Meadows |
| 6,486,212 | B2 | 11/2002 | Meinert |
| 6,489,367 | B1 | 12/2002 | Meinert |
| 6,730,328 | B2 | 5/2004 | Maskiewicz et al. |
| 7,001,607 | B1 | 2/2006 | Menz et al. |

(Continued)

FOREIGN PATENT DOCUMENTS

| | | |
|---|---|---|
| EP | 0089815 A1 | 9/1983 |
| EP | 0593552 A1 | 4/1994 |

(Continued)

OTHER PUBLICATIONS

Dutescu et al. Semifluorinated alkanes as a liquid drug carrier system for topical ocular drug delivery. European Journal of Pharmaceutics and Biopharmaceutics. vol. 88, issue 1, Sep. 2014, pp. 123-128.*

(Continued)

*Primary Examiner* — Maury A Audet

(74) *Attorney, Agent, or Firm* — Hoxie & Associates LLC

(57) ABSTRACT

The invention provides pharmaceutical compositions comprising about 0.05 to 0.1% (w/v) cyclosporine dissolved in 1-perfluorobutyl-pentane for use in the topical treatment of dry eye disease and provides for dosing and treatment methods thereof. The invention further provides kits comprising such compositions.

26 Claims, 3 Drawing Sheets

(56) References Cited

U.S. PATENT DOCUMENTS

| | | | | |
|---|---|---|---|---|
| 7,026,359 | B1 | 4/2006 | Gross et al. | |
| 7,063,241 | B2 | 6/2006 | Spada et al. | |
| 7,258,869 | B1 | 8/2007 | Berry et al. | |
| 7,740,875 | B2 | 6/2010 | Dechow | |
| 8,029,977 | B2 | 10/2011 | Meinert et al. | |
| 8,222,292 | B2 | 7/2012 | Goskonda et al. | |
| 8,328,775 | B2 | 12/2012 | Gokhale et al. | |
| 8,470,873 | B2 | 6/2013 | Chen | |
| 8,492,334 | B2 | 7/2013 | Lavik et al. | |
| 8,614,178 | B2 * | 12/2013 | Theisinger | A61K 47/06 514/1.1 |
| 8,796,340 | B2 | 8/2014 | Theisinger et al. | |
| 8,916,157 | B2 | 12/2014 | Krause et al. | |
| 8,986,738 | B2 | 3/2015 | Meinert | |
| 9,023,898 | B2 | 5/2015 | Wong et al. | |
| 9,241,900 | B2 | 1/2016 | Wilson | |
| 9,265,809 | B2 | 2/2016 | Johnson | |
| 9,278,120 | B2 | 3/2016 | Cruzat et al. | |
| 9,308,262 | B2 | 4/2016 | Günther et al. | |
| 9,757,459 | B2 | 9/2017 | Theisinger et al. | |
| 9,757,460 | B2 | 9/2017 | Günther et al. | |
| 9,770,508 | B2 | 9/2017 | Günther et al. | |
| 9,968,678 | B2 | 5/2018 | Theisinger et al. | |
| 10,004,714 | B2 | 6/2018 | Zhu et al. | |
| 10,045,996 | B2 | 8/2018 | Theisinger et al. | |
| 10,045,997 | B2 | 8/2018 | Chen et al. | |
| 10,058,615 | B2 | 8/2018 | Günther et al. | |
| 10,064,944 | B2 | 9/2018 | Wilson | |
| 10,123,904 | B2 | 11/2018 | Chauhan et al. | |
| 10,130,707 | B2 | 11/2018 | Günther et al. | |
| 10,273,298 | B2 | 4/2019 | Günther et al. | |
| 10,286,035 | B2 | 5/2019 | Gavaris | |
| 10,369,117 | B2 | 8/2019 | Günther et al. | |
| 10,449,164 | B2 | 10/2019 | Günther et al. | |
| 10,507,132 | B2 | 12/2019 | Graf et al. | |
| 10,525,062 | B2 | 1/2020 | Theisinger et al. | |
| 10,555,953 | B2 | 2/2020 | Theisinger et al. | |
| 10,576,154 | B2 | 3/2020 | Günther et al. | |
| 10,682,315 | B2 * | 6/2020 | Scherer | A61K 31/02 |
| 10,813,976 | B2 * | 10/2020 | Löscher | A61P 27/04 |
| 10,813,999 | B2 | 10/2020 | Günther et al. | |
| 11,154,513 | B2 * | 10/2021 | Scherer | A61K 31/02 |
| 11,160,865 | B2 | 11/2021 | Theisinger et al. | |
| 11,241,497 | B2 | 2/2022 | Reza et al. | |
| 11,273,174 | B2 | 3/2022 | Löscher et al. | |
| 11,278,503 | B2 | 3/2022 | Günther et al. | |
| 11,285,163 | B2 | 3/2022 | Shah et al. | |
| 11,324,757 | B2 | 5/2022 | Theisinger et al. | |
| 11,357,738 | B2 * | 6/2022 | Scherer | A61K 31/02 |
| 11,400,132 | B2 * | 8/2022 | Löscher | A61K 9/0048 |
| 11,413,323 | B2 * | 8/2022 | Leo | A61K 9/0048 |
| 11,510,855 | B2 | 11/2022 | Löscher et al. | |
| 11,576,893 | B2 | 2/2023 | Löscher et al. | |
| 11,583,513 | B2 | 2/2023 | Günther et al. | |
| 11,684,589 | B2 | 6/2023 | Günther et al. | |
| 11,723,861 | B2 | 8/2023 | Günther et al. | |
| 11,844,836 | B2 | 12/2023 | Günther et al. | |
| 11,896,559 | B2 | 2/2024 | Günther et al. | |
| 11,987,623 | B2 | 5/2024 | Günther et al. | |
| 12,005,033 | B2 | 6/2024 | Günther et al. | |
| RE50,060 | E * | 7/2024 | Graf | A61P 27/02 |
| 12,029,757 | B2 | 7/2024 | Löscher et al. | |
| 12,059,449 | B2 * | 8/2024 | Leo | A61K 9/0048 |
| 12,128,010 | B2 * | 10/2024 | Scherer | A61K 31/02 |
| 12,150,955 | B2 | 11/2024 | Löscher et al. | |
| 12,226,422 | B2 | 2/2025 | Löscher et al. | |
| 12,496,326 | B2 * | 12/2025 | Beier | A61K 38/13 |
| 2002/0004063 | A1 | 1/2002 | Zhang | |
| 2002/0128527 | A1 | 9/2002 | Meinert | |
| 2003/0018044 | A1 | 1/2003 | Peyman | |
| 2003/0027833 | A1 | 2/2003 | Cleary et al. | |
| 2003/0170194 | A1 | 9/2003 | Piotrowiak | |
| 2004/0044045 | A1 | 3/2004 | Burk | |
| 2004/0082660 | A1 | 4/2004 | Ueno | |
| 2004/0265362 | A1 | 12/2004 | Susilo | |
| 2004/0266702 | A1 | 12/2004 | Dawson et al. | |
| 2005/0079210 | A1 | 4/2005 | Gupta | |
| 2005/0175541 | A1 | 8/2005 | Lanza et al. | |
| 2005/0274744 | A1 | 12/2005 | Spada et al. | |
| 2005/0288196 | A1 | 12/2005 | Horn | |
| 2006/0153905 | A1 | 7/2006 | Carrara et al. | |
| 2008/0039807 | A1 | 2/2008 | Pine | |
| 2008/0050335 | A1 | 2/2008 | Faour et al. | |
| 2008/0153909 | A1 | 6/2008 | Dana et al. | |
| 2008/0207537 | A1 | 8/2008 | Turner et al. | |
| 2008/0234389 | A1 | 9/2008 | Mecozzi et al. | |
| 2008/0260656 | A1 | 10/2008 | Mallard | |
| 2009/0149546 | A1 | 6/2009 | Chang et al. | |
| 2010/0006600 | A1 | 1/2010 | Dascanio | |
| 2010/0008996 | A1 | 1/2010 | Meinert | |
| 2010/0016814 | A1 | 1/2010 | Gokhale et al. | |
| 2010/0028459 | A1 | 2/2010 | Kis | |
| 2010/0226997 | A1 | 9/2010 | Bowman et al. | |
| 2010/0274215 | A1 | 10/2010 | Wong et al. | |
| 2010/0279951 | A1 | 11/2010 | Morgan et al. | |
| 2011/0269704 | A1 | 11/2011 | Seigfried | |
| 2012/0010280 | A1 | 1/2012 | Aleo et al. | |
| 2012/0095097 | A1 | 4/2012 | Tabuchi et al. | |
| 2012/0238639 | A1 | 9/2012 | Theisinger et al. | |
| 2012/0244177 | A1 * | 9/2012 | Theisinger | A61K 38/13 424/185.1 |
| 2013/0046014 | A1 | 2/2013 | Theisinger et al. | |
| 2013/0084250 | A1 | 4/2013 | Hagedorn et al. | |
| 2013/0266652 | A1 | 10/2013 | Theisinger et al. | |
| 2013/0303473 | A1 | 11/2013 | Wilson | |
| 2013/0336557 | A1 | 12/2013 | Cruzat et al. | |
| 2014/0004197 | A1 | 1/2014 | Theisinger et al. | |
| 2014/0100180 | A1 | 4/2014 | Günther et al. | |
| 2014/0140942 | A1 | 5/2014 | Günther et al. | |
| 2014/0186350 | A1 | 7/2014 | Ghosh et al. | |
| 2014/0369993 | A1 | 12/2014 | Günther et al. | |
| 2015/0224064 | A1 | 8/2015 | Günther et al. | |
| 2015/0238605 | A1 | 8/2015 | Günther et al. | |
| 2016/0000941 | A1 | 1/2016 | Keller et al. | |
| 2016/0159902 | A1 | 6/2016 | Günther et al. | |
| 2016/0243189 | A1 * | 8/2016 | Gu | A61K 9/0048 |
| 2017/0020726 | A1 | 1/2017 | Labombarbe et al. | |
| 2017/0087100 | A1 | 3/2017 | Scherer et al. | |
| 2017/0087101 | A1 | 3/2017 | Scherer et al. | |
| 2017/0182060 | A1 | 6/2017 | Wiedersberg et al. | |
| 2017/0216204 | A1 | 8/2017 | Theisinger et al. | |
| 2017/0348285 | A1 | 12/2017 | Hellstrom | |
| 2018/0360908 | A1 | 12/2018 | Beier et al. | |
| 2019/0328717 | A1 | 10/2019 | Günther et al. | |
| 2021/0069014 | A1 | 3/2021 | Löscher et al. | |
| 2021/0121471 | A1 | 4/2021 | Löscher et al. | |
| 2021/0228595 | A1 | 7/2021 | Löscher et al. | |
| 2021/0315832 | A1 | 10/2021 | Scherer et al. | |
| 2021/0340248 | A1 | 11/2021 | Günther et al. | |
| 2021/0346313 | A1 | 11/2021 | Beier et al. | |
| 2022/0008397 | A1 | 1/2022 | Xu et al. | |
| 2022/0031844 | A1 | 2/2022 | Mauden et al. | |
| 2022/0079925 | A1 | 3/2022 | Günther et al. | |
| 2022/0143137 | A1 | 5/2022 | Witt et al. | |
| 2022/0152096 | A1 | 5/2022 | Löscher et al. | |
| 2022/0226426 | A1 | 7/2022 | Löscher et al. | |
| 2022/0226427 | A1 | 7/2022 | Leo et al. | |
| 2022/0354786 | A1 | 11/2022 | Friess et al. | |
| 2022/0354926 | A1 | 11/2022 | Löscher et al. | |
| 2022/0362382 | A1 | 11/2022 | Löscher et al. | |
| 2022/0370377 | A1 | 11/2022 | Scherer et al. | |
| 2023/0043641 | A1 | 2/2023 | Beier et al. | |
| 2023/0139672 | A1 | 5/2023 | Theisinger et al. | |
| 2023/0181679 | A1 | 6/2023 | Haisser et al. | |
| 2023/0330056 | A1 | 10/2023 | Günther et al. | |
| 2023/0355810 | A1 | 11/2023 | Keller et al. | |
| 2023/0398065 | A1 | 12/2023 | Günther et al. | |
| 2024/0245625 | A1 | 7/2024 | Günther et al. | |
| 2024/0350425 | A1 | 10/2024 | Günther et al. | |

FOREIGN PATENT DOCUMENTS

| | | | |
|---|---|---|---|
| EP | 0670159 | A1 | 9/1995 |
| EP | 0939655 | A1 | 9/1999 |

(56) References Cited

FOREIGN PATENT DOCUMENTS

| | | | |
|---|---|---|---|
| EP | 0965329 | A1 | 12/1999 |
| EP | 0965334 | A1 | 12/1999 |
| EP | 1152749 | A2 | 4/2006 |
| EP | 2110126 | A1 | 10/2009 |
| EP | 2332525 | A1 | 6/2011 |
| EP | 2335735 | A1 | 6/2011 |
| EP | 2462921 | A1 | 6/2012 |
| GB | 2224205 | A | 5/1990 |
| JP | S6452722 | A | 2/1989 |
| JP | 2000/511157 | A | 8/2000 |
| JP | 2001/158734 | A | 6/2001 |
| JP | 2008/505177 | A | 2/2008 |
| JP | 2011/006348 | A | 1/2011 |
| JP | 2011/024841 | A | 2/2011 |
| WO | 1995/033447 | A1 | 12/1995 |
| WO | 1996/040052 | A1 | 12/1996 |
| WO | 1997/012852 | A1 | 4/1997 |
| WO | 1998/005301 | A1 | 2/1998 |
| WO | 2000/010531 | A1 | 3/2000 |
| WO | 2000/024376 | A1 | 5/2000 |
| WO | 2000/054588 | A1 | 9/2000 |
| WO | 2002/049631 | A1 | 6/2002 |
| WO | 2004/043315 | A1 | 5/2004 |
| WO | 2005/018530 | A2 | 3/2005 |
| WO | 2005/099718 | A1 | 10/2005 |
| WO | 2005/099752 | A2 | 10/2005 |
| WO | 2005/123035 | A1 | 12/2005 |
| WO | 2006/007510 | A1 | 1/2006 |
| WO | 2006/042059 | A1 | 4/2006 |
| WO | 2006/048242 | A2 | 5/2006 |
| WO | 2007/052288 | A2 | 5/2007 |
| WO | 2008/060359 | A2 | 5/2008 |
| WO | 2009/013435 | A2 | 1/2009 |
| WO | 2009/065565 | A1 | 5/2009 |
| WO | 2010/062394 | A2 | 6/2010 |
| WO | 2010/146536 | A1 | 12/2010 |
| WO | 2011/009436 | A2 | 1/2011 |
| WO | 2011/073134 | A1 | 6/2011 |
| WO | 2012/052418 | A1 | 4/2012 |
| WO | 2012/062834 | A1 | 5/2012 |
| WO | 2012/093113 | A1 | 7/2012 |
| WO | 2012/121754 | A1 | 9/2012 |
| WO | 2012/160179 | A2 | 11/2012 |
| WO | 2012/160180 | A2 | 11/2012 |
| WO | 2013/110621 | A1 | 8/2013 |
| WO | 2014/041055 | A1 | 3/2014 |
| WO | 2014/041071 | A1 | 3/2014 |
| WO | 2014/154531 | A1 | 10/2014 |
| WO | 2016/025560 | A1 | 2/2016 |
| WO | 2016/082644 | A1 | 6/2016 |
| WO | WO 2017055453 | * | 9/2016 |
| WO | 2017/055453 | A1 | 4/2017 |
| WO | 2017/220625 | A1 | 12/2017 |
| WO | 2018/114557 | A1 | 6/2018 |
| WO | 2018/115097 | A1 | 6/2018 |

OTHER PUBLICATIONS

Topks "Semiflourinated Alkane Technology Brings Advantages for Topical Therapy" Nov. 1, 2016, Ophthamology Times, p. 1-2.*

Gehlsen et al. "Cyclosporine A using F4H5 as liquid drug carrier is effective in treating experimental dry-eye disease", Investigative Ophthalmology & Visual Science Association for Research in Vision and Ophthalmology, US, vol. 56, No. 7 (Jun. 1, 2015), see p. 319.*

Gehlsen, U. et al., "Omega-3 Fatty Acids Using F6H8-Carrier as Topical Therapy in Experimental Dry-Eye Disease," Investigative Ophthalmology & Visual Science, vol. 57, p. 417, 1 page, (2016), Abstract Only.

Gehlsen. U. et al., "Cyclosporine A using F4H5 as liquid drug carrier is effective in treating experimental dry-eye disease," Investigative Ophthalmology & Visual Science, vol. 56, No. 319, 2 pages, (2015), Abstract Only.

Gerdenitsch, A., "Emulsions—established and promising drug carriers for parenteral administration," International Pharmaceutical Industry, 2 pages, (2009) Retrieved from: http:/ipimediaworld.com/wp- content/uploads/2012/05/ Pages-from-IPI-Volume-2-Issue- I- II .pdf., Date Accessed: Jul. 20, 2016.

German, E. et al., "Reality of drop size from multi-dose eye drop bottles: is it cause for concern?" Eye, vol. 13, pp. 93-100, (1999).

Gopal, L. et al., "Use of intravitreal injection of triamcinolone acetonide in the treatment of age-related macular degeneration," Indian J Ophthalmol., vol. 55, No. 6, pp. 431-435, (2007), (8 pages).

Griffin, W., "Classification of Surface-Active Agents by 'HLB'," Journal of the Society of Cosmetic Chemists, vol. 1, pp. 311-326, (1949).

Günther, B., "Breaking the Vicious Circle of Dry Eye Disease," OIS@ SECO, Feb. 21, 2019, pp. 1-14, New Orleans, URL: https://ois.net/wp-content/uploads/2019/02/DryEye-Novaliq.pdf.

Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, vol. 239, No. 5, pp. 373-381, (2001).

Holm, R. et al., "A novel excipient, 1-perfluorohexyloctane shows limited utility for the oral delivery of poorly water-soluble drugs," European Journal of Pharmaceutical Sciences, vol. 42, pp. 416-442, (2011).

Ikervis® Prescribing Information, available at https://www.medicines.org.uk/emc/product/6937/smpc/print (Updated Mar. 2, 2022) (last accessed Apr. 27, 2023).

Ishizaki et al., "Treatment of Diabetic Retinopathy", Forum: Complication, Practice, vol. 26, No. 5, pp. 474-476, (2009).

Jonas, J. et al., "Intravitreal triamcinolone acetonide for exudative age-related macular degeneration," Br J Ophthalmol, vol. 87, pp. 462-468, (2003).

Joussen, A. et al., "The concept of heavy tamponades—chances and limitations," Graefes Arch Exp Ophthalmol, vol. 246, pp. 1217-1224, (2008).

JP 2000511157 A, English Machine Translation of the Abstract, Description, and Claims, Espacenet, Date Accessed: Feb. 10, 2016.

JPS6452722, English Machine Translation of the Abstract, Description, and Claims, Espacenet, Date Accessed: Feb. 10, 2016.

Kaercher, T. et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Kheirkhah, A. et al., "Topical 0.005% tacrolimus eye drop for refractory vernal keratoconjunctivitis," Eye (London, England), vol. 25, No. 7, pp. 872-880, (2011).

Knepp, V. et al., "Stability of Nonaqueous Suspension Formulations of Plasma Derived Factor IX and Recombinant Human Alpha Interferon at Elevated Temperatures," Pharmaceutical Research, vol. 15, No. 7, pp. 1090-1095, (1998).

Kociok, N. et al., "Influence on Membrane-Mediated Cell Activation by Vesicles of Silicone Oil or Perfluorohexyloctane," Graefe's Archive for Clinical and Experimental Ophthalmology, vol. 243, pp. 345-358, (2005).

Kumar, S. et al., "Reduction in drop size of ophthalmic topical drop preparations and the impact of treatment," Journal of Advanced Pharmaceutical Technology & Research, vol. 2, No. 3, pp. 192-194, (2011).

Lallemand, F. et al., "Cyclosporine A delivery to the eye: a pharmaceutical challenge," European Journal of Pharmaceutics and Biopharmaceutics, vol. 56, No. 3, 1 page, (2003), Abstract Only.

Lallemand, F. et al., "Cyclosporine Delivery to the Eye: A comprehensive Review of Academic and Industrial Efforts," European Journal of Pharmaceutics and Biopharmaceutics, vol. 117, pp. 14-28, (2017).

(56) References Cited

OTHER PUBLICATIONS

Lemp, M., "Management of Dry Eye Disease," The American Journal of Managed Care, vol. 14, No. 3, pp. S88-S101, (2008).
Li, Y. et al., "Limited Scleroderma (Crest Syndrome) is Associated with Worse Xerostomia and Xerophthalmia in Patients Being Evaluated for Primary Sjogren's Syndrome," Annals of Rheumatic Diseases, vol. 74, Supp. No. 2, Abstract FRI0432 (2015 Annual European Congress of Rheumatology), Jun. 12, 2015.
Lin, H. et al., "Dry eye disease: A review of diagnostic approaches and treatments," Saudi Journal of Ophthalmology, vol. 28, pp. 173-181, (2014).
Lynch, M. et al., "Reduction of Phenylephrine Drop Size in Infants Achieves Equal Dilation With Decreased Systemic Absorption," Arch Ophthalmol, vol. 105, 2 pages, (1987).
Mackiewicz, J. et al., "In Vivo Retinal Tolerance of Various Heavy Silicone Oils," Investigative Ophthalmology & Visual Science, vol. 48, No. 4, pp. 1873-1883, (2007).
Majumdar, S. et al. "A Low Concentration of Tacrolimus/Semifluorinated Alkane (SFA) Eyedrop Suppresses Intraocular Inflammation in Experimental Models of Uveitis," Current Molecular Medicine, vol. 17, No. 3, pp. 211-220, (2017).
Martín-Montañez, V. et al., "End-of-day dryness, corneal sensitivity and blink rate in contact lens wearers," Cont Lens Anterior Eye, vol. 38, No. 3, pp. 148-151, (2015).
Meinert, H. et al., "Semifluorinated Alkanes—A New Class of Compounds with Outstanding Properties for Use in Ophthalmology," European Journal of Ophthalmology, vol. 10, No. 3, pp. 189-197, (2000).
Meinert, H. et al., "The Use of Semifluorinated Alkanes in Blood-Substitutes," Biomaterials, Artificial Cells, and Immobilization Biotechnology, vol. 21, No. 5, pp. 583-595, (1993).
Messmer, E. et al. "Semifluorierte Alkane als Therapie bei Meibomdrüsen-Dysfunktion Ergebnisse einer prospektiven, multizentrischen Beobachtungsstudie," Presentation, DOG-Kongress, Sep. 29-Oct. 2, 2016, Berlin DOG (Deutsche Ophtalmologische Gesellschaft), Poster No. PSa03-02, 1 page (German language version).
Messmer, E. et al., "Semifluorinated Alkanes as a Therapy for Meibomian Gland Dysfunction Results of a prospective, multi-centered observational study," Presentation, DOG-Kongress, Sep. 29, 2016-Oct. 2, 2016, Berlin DOG (Deutsche Ophtalmologische Gesellschaft), Ophthalmologe, Aug. 2016, Poster No. PSa03-02, English Translation of Abstract, p. 138.
Messmer, E. et al., "Semifluorinated Alkanes as a Therapy for Meibomian Gland Dysfunction Results of a prospective, multi-centered observational study," Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer, E., "The Pathophysiology, Diagnosis, and Treatment of Dry Eye Disease," Deutsches Arzteblatt International, vol. 112, No. 5, pp. 71-82, (2015).
Miller, K. et al., "Minimal Clinically Important Difference for the Ocular Surface Disease Index," Socioeconomics and Health Services, Arch Ophthalmol, vol. 128, No. 1, pp. 94-101, (2010).
Moscovici, B. et al., "Clinical treatment of dry eye using 0.03% tacrolimus eye drops," Cornea, vol. 31, No. 8, pp. 945-949, (2012).
Murphy, C. et al., "Cyclosporine vs Tacrolimus Therapy for Posterior and Intermediate Uveitis," Arch Ophthalmol., vol. 123, No. 5, pp. 634-641, (2005).
Noecker, R., "Effects of Common Ophthalmic Preservatives on Ocular Health," Advances in Therapy, vol. 18, No. 5, pp. 205-215, (2001), https://doi.org/10.1007 /BF02853166.
O'Rourke, M. et al., "Enhancing Delivery of Topical Ocular Drops," Cataract & Refractive Surgery Today Europe, 2 pages, (2016).
Ohashi, Y. et al., "A randomized, placebo-controlled clinical trial of tacrolimus ophthalmic suspension 0.1% in severe allergic conjunctivitis," Journal of ocular pharmacology and therapeutics, vol. 26, No., 2, pp. 165-174 (2010).
Ozcan, A. et al., "Management of Severe Allergic Conjunctivitis With Topical Cyclosporin A 0.05% Eyedrops," Cornea, vol. 26, No. 9, pp. 1035-1038, (2007).
Pensyl, D., "Chapter 14: Preparations for Dry Eye and Ocular Surface Disease," Clinical Ocular Pharmacology, Fifth Edition, pp. 263-278, 18 pages, (2008).
Perry, H., "Dry Eye Disease: Pathophysiology, Classification, and Diagnosis," The American Journal of Managed Care, vol. 14, No. 3, pp. S79-S87, (2008).
Pflugfelder, S. et al., "The Pathophysiology of Dry Eye Disease What We Know and Future Directions for Research," Ophthalmology, vol. 124, Suppl. 11, pp. S4-S13, (2017).
Pflugfelder, S. et al., "Treatment of Blepharitis: Recent Clinical Trials," The Ocular Surface, vol. 12, No. 4, 2 pages, (2014), Abstract Only.
Pinarci, E. et al., "Intraocular Gas Application in the Diagnosis and Treatment of Valsalva Retiopathy in Case with Premacular Hemorrhage," Retina-Vitreus, vol. 17, No. 2, pp. 153-155, (2009), Abstract Only.
Plassmann, M. et al., "Theoretical and Experimental Simulation of the Fate of Semifluorinated n-Alkanes During Snowmelt," Environmental Science & Technology, vol. 44, No. 17, pp. 6692-6697, (2010).
Plassmann, M. et al., "Trace Analytical Methods for Semifluorinated n-Alkanes in Snow, Soil, and Air," Analytical Chemistry, vol. 82, No. 11, pp. 4551-4557, (2010).
Prabhu, S. et al., "Topical Cyclosporine A 0.05% for Recurrent Anterior Uveitis," Br J Opthalmol, vol. 100, No. 3, pp. 345-347, (2016), Abstract Only.
Qiao, J. et al., "Emerging treatment options for meibomian gland dysfunction," Clinical Ophthalmology, vol. 7, pp. 1797-1803, (2013).
RESTASIS® Prescribing Information, available at https://www.accessdata.fda.gov/drugsatfda_docs/label/2012/050790s020lbl.pdf(Nov. 2012) (last accessed Feb. 28, 2023).
Rojas-Carabali, W. et al. "Clinical relationships between dry eye disease and uveitis: a scoping review," Journal of Ophthalmic Inflammation and Infection, vol. 13, No. 2, (2023).
Sall, K. et al., "Two Multicenter, Randomized Studies of the Efficacy and Safety of Cyclosporine Ophthalmic Emulsion in Moderate to Severe Dry Eye Disease," Ophthalmology, vol. 107, No. 4, pp. 631-639, (2000).
Santvliet, L. et al., "Determinants of Eye Drop Size," Survey of Ophthalmology, vol. 49, No. 2, pp. 197-213, (2004).
Sato, N. et al., "Vitrectomy and Intraocular Lens Implantation for Cytomegalovirus Retinitis in a Patient with Acquired Immunodeficiency Syndrome", Presented by Medical Online, New Ophthalmology, vol. 16, Nol. 7, pp. 995-998, (1999).
Scherer, D. et al., "Eyesol: A Novel Topical Ocular Drug Delivery System for Poorly Soluble Drugs," Drug Development & Delivery, vol. 13, No. 1, pp. 40-44, (2013).
Schmitt, M., "Chapter 10: Design and Development of Ocular Formulations for Preclinical and Clinical Trials," Innovative Dosage Forms: Design and Development at Early Stage, pp. 331-365, 35 pages, (2020).
Schmutz, M. et al., "Fluorinated Vesicles Made from Combinations of Phospholipids and Semifluorinated Alkanes. Direct Experimental Evidence of the Location of the Semifluorinated Alkane within the Bilayer," Langmuir, vol. 19, pp. 4889-4894, (2003).
Schnetler, R. et al., "Lipid composition of human meibum: a review", S Afr Optom, vol. 72, No., 2, pp. 86-93, (2013).
Sheppard, J. et al., "A Water-free 0.1% Cyclosporine A Solution for Treatment of Dry Eye Disease: Results of the Randomized Phase 2B/3 Essence Study," Cornea, vol. 40, No. 10, pp. 1290-1297, (2021).
Spöler, F. et al., "Towards a New in vitro Model of Dry Eye: The ex vivo Eye Irritation Test," Developments in Ophthalmology, vol. 45, pp. 93-107, (2010).
Steven, P. et al., "Semifluorinated Alkane Eye Drops for Treatment of Dry Eye Disease—A Prospective, Multicenter Noninterventional Study" Investigative Ophthalmology & Visual Science, vol. 56, No. 4493, 1 page, (2015), Abstract Only.

(56) References Cited

OTHER PUBLICATIONS

Steven, P. et al., "Semifluorinated Alkane Eye Drops for Treatment of Dry Eye Disease—A Prospective, Multicenter Noninterventional Study," Journal of Ocular Pharmacology and Therapeutics, vol. 31, No. 8, pp. 498-503, (2015).
Steven, P. et al., "Semifluorinated Alkane Eye Drops for Treatment of Dry Eye Disease Due to Meibomian Gland Disease," Journal of Ocular Pharmacology and Therapeutics, vol. 33, No. 9, pp. 1-8, (2017).
Tamura, S. et al., "Tacrolimus is a class II low-solubility high-permeability drug: The effect of P-glycoprotein efflux on regional permeability of tacrolimus in rats," Journal of Pharmaceutical Sciences, vol. 91, No. 3, pp. 719-729, 1 page, (2002), Abstract Only.
Tauber, J. et al., "A Randomized Clinical Study (SEECASE) to Assess Efficacy, Safety, and Tolerability of NOV03 for Treatment of Dry Eye Disease," Cornea, vol. 40, No. 9 , pp. 1132-1140, (2021).
Tiffany, J., "Individual Variations in Human Meibomian Composition," Exp. Eye Res., vol. 27, pp. 289-300, (1978).
Torkildsen, G. et al., "A Clinical Phase 2 Study to Assess Safety, Efficacy, and Tolerability of CyclASol for the Treatment of Dry Eye Disease," Poster Presentation at American Academy of Ophthalmology (AAO), New Orleans 2017.
Troiano, P. et al., "Effect of Hyptonic .4% Hyaluronic Acid Drops in Dry Eye Patients: A Cross-Study," Cornea, vol. 27, No. 10, pp. 1126-1130, (2008), Abstract Only.
Utine, C. et al., "Clinical Review: Topical Ophthalmic Use of Cyclosporin A," Ocular Immunology & Inflammation, vol. 18, No. 5, pp. 352-361, (2010).
Wirta, D. et al., "A Clinical Phase II Study to Assess Efficacy, Safety and Tolerability of Waterfree Cyclosporine Formulation for the Treatment of Dry Eye Disease," Ophthalmology, vol. 126, pp. 792-800, (2019).
Wong, D. et al., "Perfluorocarbons and Semifluorinated Alkanes," Seminars in Ophthalmology, vol. 15, No. 1, pp. 25-35, (2000).
Xalatan, Latanoprost Ophthalmic Solution, 50 μg/mL Prostaglandin F 2α analogue, Product Monograph, Jul. 21, 2014, 30 pages.
Xu, H. et al., "A Clinical Grading System for Retinal Inflammation in the Chronic Model of Experimental Autoimmune Uveoretinitis Using Digital Fundus Images," Experimental Eye Research, vol. 87, No. 4, pp. 319-326, (2008).
Yaoxue Zhuanye Zhishi II (Editor: Jin Xiangqun), Military Medical Science Press, 1st Printing of 2nd Edition, Mar. 2009, p. 158.
Yaoxue Zhuanye Zhishi II (Editor: Jin Xiangqun), Military Medical Science Press, 1st Printing of 2nd Edition, Mar. 2009, p. 158, 3 pages, English Machine Translation.
Yazu, H. et al., "The efficacy of 0.1% tacrolimus ophthalmic suspension in the treatment of severe atopic keratoconjunctivitis," Annals of allergy, asthma & immunology, vol. 122, No. 4, pp. 387-392 (2019).
Zeev, M. et al., "Diagnosis of dry eye disease and emerging technologies," Clinical Ophthalmology, vol. 8, pp. 581-590, 11 pages, (2014).
Zeng, Y., "Atlas of Clinical Keratoconjunctival Disease," Hubei Science and Technology Press, pp. 287-299, (2011).
Zeng, Y., "Atlas of Clinical Keratoconjunctival Disease," Hubei Science and Technology Press, pp. 287-299, (2011), English Translation.
Zhang, G. et al., "Surface micelles of semifluorinated alkanes in Langmuir-Blodgett monolayers," Phys. Chem. Chem. Phys., vol. 6, pp. 1566-1569, (2004).
Zhang, X. et al., "Dry Eye Management: Targeting the Ocular Surface Microenvironment," International Journal of Molecular Sciences, vol. 18, pp. 1398, 28 pages, (2017).
"EvoTears—Gebrauchsanweisung," May 2015, retrieved from the Internet, date retrieved: Jun. 26, 2018, 2 pages, URL: http://video.apo-rot.de/docs/11213615.pdf.
"EvoTears, Product Description," 2017, Accessed Online: Dec. 27, 2023, URL: https://evotears.com/at/das-produkt/.
"Keratoconjunctivitis," Cleveland Clinic, last updated Jul. 8, 2022, downloaded from https://my.clevelandclinic.org/health/diseases/23551-keratoconjunctivitis.
"Novaliq Announces Positive Topline Results of Phase 2 Clinical Trial Evaluating CyclASol® in Adults with Moderate to Severe Dry Eye Disease," Businesswire, Jan. 5, 2017, URL: <https://www.businesswire.com/ news/home/20170105005211/en/Novaliq-Announces-Positive-Topline-Results-Phase-2>.
"Novaliq begins Phase 2 trial of Cyclasol for dry eye disease," Optometry Times, vol. 8, No. 3, (2016), p. 24.
"Novaliq GmbH Begins Phase II Clinical Trial of Cyclasol for the Treatment of Moderate to Severe Dry Eye Disease," (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.
"Ocular Surface Disease Index (OSDI)", Dec. 1, 2003, pp. 1-2, Retrieved from the Internet: URL: http://www.supereyecare.com/resources/OSDI.pdf.
"PharmaNews," Kompass Ophthalmologie, vol. 2, No. 2, pp. 98-99, (2016).
"Semifluorinated alkane technology brings advantages for topical therapy," Ophthalmology Times, 2016, pp. 1-2.
"Topical drug dosage forms for eye conditions," The Pharmaceutical Journal, (Pharmaceutical Press, May 31, 2017), available at https://pharmaceutical-journal.com/article/Id/topical-drug-dosage-forms-for-eye-conditions.
"What is retinal vitrectomy?" Presented by: Medical Online, Obesity and Diabetes Mellitus, vol. 4, No. 2, pp. 284-286, 3 pages, (2005).
"Xerophthalmia," Eye Clinic, 4 pages, archived Dec. 30, 2014.
Agarwal, P. et al., "Modern Approaches to the Ocular Delivery of Cyclosporine A," Drug Discovery Today, vol. 21, No. 6, pp. 977-988, (2016), doi: 10.1016/j.drudis.2016.04.002.
Agarwal, P. et al., "Semifluorinated alkane based systems for enhanced corneal penetration of poorly soluble drugs," International Journal of Pharmaceutics, vol. 538, No. 1-2, pp. 119-129, (2018).
Agrahari, V. et al., "A comprehensive insight on ocular pharmacokinetics," Drug Delivery and Translational Research, vol. 6, No. 6, pp. 735-754, (2016).
Ahmed, I. et al., "Disposition of Timolol and Inulin in the Rabbit Eye Following Corneal Versus Non-Corneal Absorption," International Journal of Pharmaceutics, vol. 38, pp. 9-21, (1987).
Ahmed, S. et al., "Ocular Drug Delivery: a Comprehensive Review," AAPS PharmSciTech, vol. 24, No. 66, pp. 1-29, (2023).
Al-Amri, A. et al., "Long-term use of 0.003% tacrolimus suspension for treatment of vernal keratoconjunctivitis," Oman Journal of Ophthalmology, vol. 10, No. 3, pp. 145-149, (2017).
Ann Marie Griff, O.D., & Ann Pietrangelo, "Everything you need to know about keratoconjunctivitis," Healthline.com, Nov. 22, 2019, downloaded from https://www.healthline.com/health/keratoconjunctivitis.
Babu, K. et al., "Medical Management of Uveitis—Current Trends," Indian J Opthalmol., vol. 61, No. 6, pp. 277-283, (2013).
Baerdemaeker, L. et al., "Pharmacokinetics in Obese Patients," Continuing Education in Anaesthesia, Critical Care & Pain, vol. 4, pp. 152-155, (2004).
Barata-Vallejo, S. et al., "(Me3Si)3SiH-Mediated Intermolecular Radical Perfluoroalkylation Reactions of Olefins in Water," J. Org. Chem., vol. 75, pp. 6141-6148, (2010).
Bardin, L. et al., "Long-Range Nanometer-Scale Organization of Semifluorinated Alkane Monolayers at the Air/Water Interface," Langmuir, vol. 27, p. 13497-13505, (2011).
Benezra, D. et al., "Cyclosporine eyedrops for the treatment of severe vernal keratoconjunctivitis," American Journal of Ophthalmology, vol. 101, pp. 278-282, (1986).
Bhargava, A. et al., "Ocular Allergic Disease," Drugs of Today/Medicamentos de Actualidad, J.R. Prous SS.A. International Publishers, vol. 34, No. 11, pp. 957-971, (1998).
Blackie, C. et al., "Getting to the Root Cause of Dry Eye," Review of Optometry, 12 pages, (2012).

(56) References Cited

OTHER PUBLICATIONS

Bron, A. et al., "Grading of Corneal and Conjunctival Staining in the Context of Other Dry Eye Tests," Cornea, vol. 22, No. 7, pp. 640-650, (2003).
Broniatowski, M. et al., "Langmuir Monolayers Characteristic of (Perfluorodecyl)-Alkanes," Journal of Physical Chemistry B, vol. 108, pp. 13403-13411, (2004).
Cabral, T. et al., "Retinal and choroidal angiogenesis: a review of new targets," International Journal of Retina and Vitreous, vol. 3, No. 31, (2017).
CEQUA® Prescribing Information, available at https://www.accessdata.fda.gov/drugsatfda_docs/label/2018/210913s000lbl.pdf (Aug. 2018) (last accessed Feb. 28, 2023).
Chaglasian, E. et al., "Recycling Cyclosporine," Review of Cornea & Contact Lenses, 2016, 5 pages.
Chao, W. et al., "Report of the Inaugural Meeting of the TFOS i2 = initiating innovation Series: Targeting the Unmet Need for Dry Eye Treatment," (London, United Kingdom, Mar. 21, 2015) Accepted Manuscript, Accepted Date: Nov. 11, 2015, 94 pages.
Chhadva, P. et al., "Meibomian Gland Disease: The Role of Gland Dysfunction in Drye Eye Disease," Ophthalmology, vol. 124, Suppl. 11, pp. S20-S26, (2017).
Costa Gomes, M. et al., "Solubility of dioxygen in seven fluorinated liquids," Journal of Fluorine Chemistry, vol. 125, pp. 1325-1329, (2004).
Daull, P. et al., "Distribution of Cyclosporine A in Ocular Tissues After Topical Administration of Cyclosporine A Cationic Emulsions to Pigmented Rabbits," Cornea, vol. 32, No. 3, pp. 345-354, (2013), Abstract Only.
Davies, N., "Biopharmaceutical Considerations in Topical Ocular Drug Delivery," Clinical and Experimental Pharmacology and Physiology, vol. 27, pp. 558-562, (2000).
Del Amo, E., "Topical ophthalmic administration: Can a drug instilled onto the ocular surface exert an effect at the back of the eye?" Frontiers in Drug Discovery 2:954771 (Sep. 8, 2022), available at https://www.frontiersin.org/articles/10.3389/fddev.2022.954771/full.
Dembinski, R. et al., "Semi-fluorinated Alkanes as Carriers for Drug Targeting in Acute Respiratory Failure," Experimental Lung Research, vol. 36, pp. 499-507, (2010).
Deschamps, J. et al., "Solubility of oxygen, carbon dioxide and water in semifluorinated alkanes and in perfluorooctylbromide by molecular simulation," Journal of Fluorine Chemistry, Elsevier, vol. 125, No. 3, (2004).
Dias, A. et al., "Solubility of oxygen in liquid perfluorocarbons," Fluid Phase Equilibria, vol. 222-223, pp. 325-330, (2004).
Dutescu, R. et al., "Semifluorinated alkanes as a liquid drug carrier system for topical ocular drug delivery," European Journal of Pharmaceutics and Biopharmaceutics, vol. 88, No. 1, pp. 123-128, (2014).
English language machine translation for "PharmaNews," Kompass Ophthalmologie, vol. 2, No. 2, pp. 98-99, (2016).
English-language machine translation of EP0670159 (A1) issued in U.S. Appl. No. 14/122,025 on Apr. 1, 2015, 10 pages.
Eom, Y. et al., "Comparison of Meibomian Gland Loss and Expressed Meibum Grade Between the Upper and Lower Eyelids in Patients With Obstructive Meibomian Gland Dysfunction," Cornea, vol. 33, No. 5, 6 pages, (2014).
Foulks, G. et al., "Improving Awareness, Identification, and Management of Meibomian Gland Dysfunction," Ophthalmology, Supplement, vol. 119, No. 10, pp. S1-S12, (2012), https://doi.org/10.1016/j.ophtha .2012.06.064.
Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.
Ganka, A., "Definition and Diagnostic Criteria for Meibomian Gland Dysfunction," Journal of Ophthalmology, vol. 27, No. 5, pp. 627-631, 6 pages, (2010), Abstract only.
Garg, V. et al., "Topical tacrolimus nanoemulsion, a promising therapeutic approach for uveitis," Medical Hypotheses, vol. 81, pp. 901-904, (2013).
Gayton, J., "Etiology, Prevalence, and Treatment of Dry Eye Disease," Clinical Ophthalmology, vol. 3, pp. 405-412, (2009).
Gehlsen, U. et al., "A semifluorinated alkane (F4H5) as novel carrier for cyclosporine A: a promising therapeutic and prophylactic option for topical treatment of dry eye," Graefe's Arch. Clin. Exp. Ophthalmol., vol. 255, No. 4, pp. 767-775, (2017).

* cited by examiner

OPHTHALMIC COMPOSITION FOR TREATMENT OF DRY EYE DISEASE

CROSS-REFERENCE TO RELATED APPLICATIONS

This application is a continuation of U.S. application Ser. No. 17/933,471, filed on Sep. 19, 2022, which is a division of U.S. application Ser. No. 16/109,127, filed on Aug. 22, 2018, which is a continuation application of International Application No. PCT/EP2017/083770, filed Dec. 20, 2017, which claims priority to, and the benefit of, European Application No. 16206735.9, filed Dec. 23, 2016, and European Application No. 17165578.0, filed Apr. 7, 2017, the contents of each of which are incorporated herein by reference in their entireties.

BACKGROUND OF THE INVENTION

Keratoconjunctivitis sicca, also known as dry eye disease or dysfunctional tear syndrome, is today understood as a multifunctional disorder of the tear film and of the ocular surface which results in discomfort, visual disturbance, and often even in ocular surface damage caused by tear film instability. Estimates of the prevalence of dry eye vary considerably, depending on the criteria used to define the disease, but in the U.S., it has been estimated that as many as 3.2 million women and 1.7 million men over the age of 50 have dry eye, with a projected 40% increase in number of patients affected by 2030.

A pharmacological treatment option for dry eye disease is cyclosporine. Cyclosporine is available, at least in the US as an approved medicine in the form of an ophthalmic (o/w) emulsion (Restasis®). This product is indicated to increase tear production in patients whose tear production is presumed to be suppressed due to ocular inflammation associated with keratoconjunctivitis sicca.

WO2011/073134 A1 discloses pharmaceutical compositions in the form of solutions comprising cyclosporine and a semifluorinated alkane as a liquid vehicle which may be administered to the eye of a patient, such as for the treatment of keratoconjunctivitis sicca, for instance compositions comprising cyclosporine in semifluorinated alkane 1-perfluorobutyl-pentane (F4H5) in the presence of ethanol as a co-solvent. WO2011/073134 A1 however does not describe dosing and treatment regimen for the treatment of dry eye disease, in particular moderate to severe dry eye disease and associated conditions.

Gehlsen et al. (Investigative Ophthalmology & Visual Science June 2015, Vol. 56, 319) describes a study to test the use of CsA in SFA (F4H5) as a carrier for topical therapy in a mouse model of experimental dry eye disease. Gehlsen et al describes that in the study, topical therapy was performed on mice with induced experimental dry eye disease 3×/day (5 μL/eye). Gehlsen et al, however does not disclose a treatment or dosing regimen for the treatment of dry eye disease in human subjects, in particular subjects with moderate to severe dry eye disease and associated conditions.

It is thus an object of the present invention to provide pharmaceutical compositions for use in the treatment of dry eye disease, in particular moderate to severe dry eye disease and associated conditions comprising cyclosporine and 1-perfluorobutyl-pentane. Further objects of the invention will be clear on the basis of the following description of the invention, examples and claims.

SUMMARY OF THE INVENTION

In a first aspect, the invention relates to a pharmaceutical composition for use in the topical treatment of dry eye disease, wherein the composition comprises about 0.05 to 0.1% (w/v) cyclosporine dissolved in 1-perfluorobutyl-pentane and wherein the amount of cyclosporine administered in a single dose per eye is about 4 to 12 μg.

In a further aspect, the present invention provides pharmaceutical compositions for use in the treatment of ocular surface damage in subjects suffering from dry eye disease, and/or for use in the treatment of reading impairment in subjects suffering from dry eye disease, preferably wherein the pharmaceutical compositions are topically administered to provide an amount of about 4 to 12 μg of cyclosporine per single dose per eye. In particular, the subjects may have moderate to severe dry eye disease, In yet a further aspect, the invention provides for a kit comprising a pharmaceutical composition for such uses, wherein the kit comprises a container for holding the pharmaceutical composition and a drop dispenser adapted for administering about 8 to 12 μl volume of the composition per drop.

DETAILED DESCRIPTION OF THE INVENTION

The present invention relates to, in a first aspect, a pharmaceutical composition for use in the topical treatment of dry eye disease, wherein the composition comprises about 0.05 to 0.1% (w/v) cyclosporine dissolved in 1-perfluorobutyl-pentane and wherein the amount of cyclosporine administered in a single dose per eye is about 4 to 12 μg.

Dry eye disease (also abbreviated as DED, and which also may be known as keratoconjunctivitis sicca, dysfunctional tear syndrome or dry eye syndrome) is a complex disease that results in symptoms of discomfort, visual disturbance, and tear film instability, and which creates potential for damage of the ocular surface. It may be accompanied by increased osmolarity of the tear film and inflammation of the ocular surface. A patient having keratoconjunctivitis sicca may experience any one of, or a combination of tear hyperosmolarity, tear film instability or abnormalities in the lipid layer composition of the tear film.

Two major categories of keratoconjunctivitis sicca or dry eye disease (DED) are distinguished today, which are aqueous-deficient DED and evaporative DED. Within the class of aqueous-deficient forms of DED, two major subtypes may be differentiated, Sjögren and non-Sjögren.

Sjögren syndrome patients suffer from autoimmune disorders in which the lacrimal glands are invaded by activated T-cells, which leads not only to dry eye disease but also to a dry mouth condition. The Sjögren syndrome can be a primary disease or result from other autoimmune diseases such as systemic lupus erythrematosus or rheumatoid arthritis. Non-Sjögren patients suffering from an aqueous-deficient DED usually have a lacrimal gland insufficiency, lacrimal duct obstruction or reflex hyposecretion.

The second major class, evaporative dry eye disease, is also somewhat heterogeneous and can develop as a result of diverse root causes. One of the major causes is meibomian gland disease or dysfunction, eyelid aperture disorders, blink disorders (as in Parkinson disease) or ocular surface disorders (as in allergic conjunctivitis).

Symptoms of dry eye disease may include, but are not limited to any one, or combination of the following: a dry, scratchy, gritty, or sandy feeling in the eye; foreign body sensation; pain or soreness; stinging or burning; itching; increased blinking; eye fatigue; photophobia; blurry vision; redness; mucus discharge; contact lens intolerance; and excessive reflex tearing. It is understood that not all patients suffering from dry eye disease may exhibit all of these symptoms simultaneously.

As understood herein, the term "dry eye disease" individually may refer to any one or combination of the subtypes or categories, or root causes as described herein and that any symptom or aspect or pathophysiological consequences of dry eye disease may be addressed.

Cyclosporine is a pharmacological treatment option for dry eye disease, which is available as a prescription medication, for example in the US in the form of an 0.05% ophthalmic (o/w) emulsion (Restasis®). This product is indicated to increase tear production in patients whose tear production is presumed to be suppressed due to ocular inflammation associated with keratoconjunctivitis sicca. Restasis® is administered twice a day in each eye approximately 12 hours apart. It is packaged in single-vials. (Prescribing Information, Restasis®).

Cyclosporine (synonyms include cyclosporin A, CsA, or ciclosporin) is a cyclic nonribosomal peptide comprising 11 amino acids with the empirical formula $C_{62}H_{111}N_{11}O_{12}$ and molecular weight of 1202.61. It is an immunosuppressant drug that is widely used in post-allergenic organ transplant, to reduce the activity of the patient's immune system and thereby, the risk of organ rejection. Cyclosporine is typically provided as a colourless or white powder. Cyclosporine is thought to bind to the cytosolic protein cyclophilin (immunophilin) of immunocompetent lymphocytes, especially T-lymphocytes. This complex of cyclosporin and cyclophilin inhibits calcineurin, which, under normal circumstances, is responsible for activating the transcription of interleukin 2. It also inhibits lymphokine production and interleukin release and, therefore, leads to a reduced function of effector T-cells.

The pharmaceutical composition according to the present invention employs, as a liquid vehicle for the cyclosporine, the compound 1-perfluorobutyl-pentane. 1-perfluorobutyl-pentane is a semifluorinated alkane with the chemical formula $F(CF_2)_4(CH_2)_5H$. It is an inert, water-insoluble liquid, with a density of 1.284 g/cm$^3$ at 25° C. and refractive index of 1.3204 at 20° C. Alternative nomenclature for this compound includes F4H5, wherein F denotes a linear perfluorinated alkane segment comprising 4 carbon atoms and wherein H denotes a linear and non-fluorinated alkane hydrocarbon segment of 5 carbon atoms. Preferably, the 1-perfluorobutyl-pentane is substantially free of water.

In one embodiment, the pharmaceutical composition for use according to the present invention may comprise or consist, further to the cyclosporine featured in any one the preferred concentrations of the invention, of at least about 97% (w/w) or more preferably, of at least about 98% (w/w), or of at least about 99% (w/w) of 1-perfluorobutyl-pentane, based on the total weight of the final pharmaceutical composition (final dosage form). In another embodiment, the pharmaceutical composition for use according to the present invention may consist of, in addition to the cyclosporine in an amount or concentration as defined herein, from about 95.0 to about 99.99% (w/w), or about 96.0 to about 99.99% (w/w), or from about 98.0 to 99.99% (w/w), or from about 99.999 to about 99.9999% (w/w) of 1-perfluorobutyl-pentane, based on the total weight of the final composition.

In another embodiment, the pharmaceutical composition of the present invention may optionally further comprise 2-perfluorobutyl-pentane. Preferably the composition, in addition to 1-perfluorobutyl-pentane, may optionally comprise minor amounts of 2-perfluorobutyl-pentane of up to 2% (w/w), or up to 1% (w/w), or most preferably, of up to 0.5% (w/w).

The concentration of cyclosporine in the pharmaceutical compositions for use according to the invention are in the range of about 0.05 to 0.1% (w/v) of the composition. Preferably, the concentration of cyclosporine in the composition is about 0.05% (w/v) or about 0.1% (w/v).

Unless otherwise indicated, the term "% (w/v)" denotes the amount of a component of a composition as a weight percentage in relation to the total volume of the composition (with 'w' denoting the weight and 'v' denoting volume). For example 0.05% (w/v) may be understood as relating to 0.5 mg of a component in 1 mL of the composition, and 0.1% (w/v) would correspond to 1.0 mg of a component in 1 mL of the composition. Unless otherwise indicated, the term "% (w/w)" refers to the amount of a component of a composition as a weight percentage in relation to the total weight of the composition (with 'w' denoting weight).

The term 'about' as used herein and in reference or connection to a parameter, for example such as the concentration of cyclosporine dissolved in the composition or the amount of cyclosporine featured in a single dose of the composition includes the precise value as defined, as well as any value falling within the degree of variability usually observed in measuring or determining these parameters using the standard techniques and equipment known in the art and field.

In respect of the amount of cyclosporine administered for the topical treatment of dry eye disease, the preferred dosage of the pharmaceutical composition is about 4 to 12 μg of cyclosporine per single dose per eye. In another embodiment, the topically administered single dose per eye may be about 5 to 10 μg, or more preferably, about 5 μg or about 10 μg.

Preferably, the total daily dosage of cyclosporine administered per eye of a pharmaceutical composition according to the invention is about 8 to 24 μg per day, or more preferably, about 10 to 20 μg per day, or even more preferably, about 10 μg or 20 μg per day.

In a preferred embodiment of the invention in respect of treatment of dry eye disease, about 5 μg of cyclosporine is administered per single dose per eye, of a pharmaceutical composition comprising 0.05% (w/v) of cyclosporine dissolved in 1-perfluorobutyl-pentane, and optionally up to about 1.0% (w/w) ethanol.

In a further preferred embodiment of the invention in respect of topical treatment of dry eye disease, about 10 μg of cyclosporine is administered per single dose per eye, of a pharmaceutical composition comprising 0.1% (w/v) of cyclosporine dissolved in 1-perfluorobutyl-pentane, and optionally up to about 1.0% (w/w) ethanol.

In yet a further embodiment, the total daily administered dose per eye of the pharmaceutical composition for use as described in any of the embodiments according to the invention is less than about 28 μg. Preferably, the total daily administered dose per eye does not exceed about 24 μg. Even more preferably, the total daily administered dose per eye does not exceed about 20 μg, or about 10 μg.

It is further preferred, that the amount of a single dose per eye of cyclosporine of the pharmaceutical composition for use in the topical treatment of dry eye disease, comprising about 0.05 to 0.1% (w/v) cyclosporine dissolved in 1-perfluorobutyl-pentane, optionally up to about 1.0% (w/w) ethanol, is administered in a volume of about 8-12 μl, preferably in a volume of about 10 μl.

It is even further preferred that the amount of a single dose per eye of cyclosporine of the pharmaceutical composition for use in the topical treatment of dry eye disease comprising about 0.05% (w/v) cyclosporine dissolved in 1-perfluorobutyl-pentane, and optionally, up to about 1.0% (w/w) ethanol, is administered in a volume of about 8-12 μl, preferably in a volume of about 10 μl.

It is even further preferred that the amount of a single dose per eye of cyclosporine of the pharmaceutical composition for use in the topical treatment of dry eye disease comprising about 0.1% (w/v) cyclosporine dissolved in 1-perfluorobutyl-pentane and optionally, up to about 1.0% (w/w) ethanol, is administered in a volume of about 8-12 μl, preferably in a volume of about 10 μl.

It has been found that treatment of subjects with dry eye disease with the pharmaceutical compositions according to the invention and at the defined doses surprisingly provided a reduction in dry eye disease indicators such as corneal and conjunctival staining and patient questionnaire (See Example, FIG. 2-4), at improved levels over the comparator product, which was administered at its prescribed dose. Subjects receiving and treated with a pharmaceutical composition according to the invention were exposed to a daily dose of cyclosporine per eye that approximately 30-65% less than the comparator cyclosporine product. An earlier onset of effect, already in the first 2 to 4 weeks of treatment was also observed. It was also shown that CyclASol 0.05% and CyclASol 0.1% (ref. Example) have excellent safety profiles, with high tolerability and patient acceptance.

The reduction in required dosing may be advantageous in that less of the active ingredient is required to reach the treatment objective. This may potentially also be beneficial in lessening adverse effect or reactions associated with cyclosporine in subjects such as for those who may require longer term treatment.

It was found that treatment of subjects with dry eye disease with the pharmaceutical compositions according to the invention and at the defined doses surprisingly did result not only in a reduction of the total adverse effects (also referred to as adverse events), but also in particular to a reduction of ocular adverse effects, namely a reduction of eye irritation, blurred vision, conjunctival haemorrhage, conjunctivitis and a reduction in instillation site pain, especially a reduction of eye irritation, blurred vision and a reduction in instillation site pain, when compared to the 0.05% cyclosporine aqueous (o/w) emulsion (Restasis). With the reduction in occurrence of adverse events, in particular ocular adverse effects as noted above, the pharmaceutical compositions are found to be safe, well tolerated and comfortable to the eye of the human and suitable for use in the methods of treatment as described herein.

The pharmaceutical compositions as defined herein are not only preferably used for the treatment of subjects with dry eye disease, but also for specific conditions associated there with, and also in particular for subjects with moderate to severe dry eye disease.

A further aspect of the present invention relates to a pharmaceutical composition for use in the treatment of reading impairment in a subject suffering from dry eye disease, wherein the composition comprises about 0.05 to 0.1% (w/v) cyclosporine dissolved in 1-perfluorobutyl-pentane. The treatment involves topical administration of said composition to an eye or eyes of a subject suffering from dry eye disease and who as a result has difficulties in reading.

Subjects suffering from dry eye disease may experience symptoms which individually, or collectively, such as blurring, pain, irritation or corneal surface damage such as to the central cornea, which may contribute to visual impairment or difficulties which can be reflected by a negative effect on the subject's performance in functional tasks where visual performance and acuity may be essential. In particular, subjects suffering from dry eye disease may experience symptoms which individually or collectively may contribute to poorer quality of vision or ocular comfort which results or contributes to difficulties in reading and overall reduction in reading performance. Reading impairment may be caused by increased ocular discomfort during, or as a consequent to the task of reading (for example heightened symptoms of any one of the dry eye disease symptoms referenced herein), and/or difficulty in visualizing or perceiving characters while reading, for instance due to blurred vision or a high frequency of blinking.

Dry eye disease patients with a reading impairment may have a score of at least equal to, or greater than about 1.0 on the OSDI question relating to reading. Question 6 of the OSDI questionnaire assesses a subject's problems with their eyes during the week preceding the assessment in terms of their reading ability with a scoring of 0 to 4 (0 for none of the time, 1 for some of the time, 2 for half of the time, 3 for most of the time and 4 for all of the time). Reading impairment may also be assessed by parameters such as a subject's reading speed or acuity (e.g. with silent or reading out loud) of a standard text.

In a preferred embodiment, the invention relates to a pharmaceutical composition for use in the treatment of reading impairment in a subject suffering from dry eye disease, wherein the composition comprises about 0.05 to 0.1% (w/v) cyclosporine dissolved in 1-perfluorobutyl-pentane and optionally up to about 1.0% (w/w) of ethanol; and wherein the amount of cyclosporine administered in a single dose per eye is about 4 to 12 μg.

In a further preferred embodiment, such pharmaceutical composition may be used in the treatment of reading impairment in a subject suffering from moderate to severe dry eye disease, and preferably wherein the composition is administered twice daily, or wherein the total daily administered dose is less than about 28 μg per eye, or preferably, wherein the daily administered dose does not exceed about 24 μg. Even more preferably, the total daily administered dose per eye is below about 20 μg, or below about 10 μg.

In another embodiment, the topically administered single dose per eye used in the treatment of reading impairment in subjects suffering from dry eye disease may be about 5 to 10 μg, or more preferably, about 5 μg or about 10 μg.

In a further preferred embodiment of the invention in respect of the treatment of reading impairment in subjects suffering from dry eye disease, about 5 μg of cyclosporine is administered per single dose per eye, of a pharmaceutical composition comprising 0.05% (w/v) of cyclosporine dissolved in 1-perfluorobutyl-pentane, and optionally up to about 1.0% (w/w) ethanol.

In yet a further preferred embodiment of the invention in respect of the treatment of reading impairment in subjects suffering from dry eye disease, about 10 μg of cyclosporine is administered per single dose per eye, of a pharmaceutical composition comprising 0.1% (w/v) of cyclosporine dissolved in 1-perfluorobutyl-pentane, and optionally up to about 1.0% (w/w) ethanol.

A reading impairment can introduce difficulties in many tasks in daily life and employment where such function is important, and may lead to reduction in work productivity and performance. It has been found unexpectedly that topical ophthalmic treatment, utilizing the compositions of the present invention, of patients suffering from dry eye disease, preferably moderate to severe category may lead to improvement in scoring for reading impairment (such as from the OSDI ref. FIG. 4).

In particular, it has been found that reading impairment in patients suffering from (moderate to severe) dry eye disease treated via topical administration of a pharmaceutical composition as described herein in the described amounts and dosing methods, may lead to a reduction in the scoring of the reading impairment (such as OSDI) by at least about 15%, or at least about 25%, or at least about 30%.

In another aspect, the invention relates to a pharmaceutical composition for use in the treatment of ocular surface damage in a subject suffering from dry eye disease, wherein the composition comprises about 0.05 to 0.1% (w/v) cyclosporine dissolved in 1-perfluorobutyl-pentane and wherein the amount of cyclosporine administered in a single dose per eye is about 4 to 12 μg.

In further aspect, the invention relates to a pharmaceutical composition for use in the treatment of ocular surface damage selected from corneal and/or conjunctival damage in a subject suffering from dry eye disease, wherein the composition comprises about 0.05 to 0.1% (w/v) cyclosporine dissolved in 1-perfluorobutyl-pentane, and wherein the amount of cyclosporine administered in a single dose per eye is about 4 to 12 μg.

Damage to the cornea and associated tissues is prevalent in patients with dry eye disease, in particular those with moderate to severe, or severe dry eye disease. The tear film, with its lipid, aqueous and mucin layers normally provides a protective barrier to corneal tissue and corneal epithelium and has a wetting function i.e. prevents drying/desiccation. It acts as a conduit for the provision of oxygen and nutrients to the corneal epithelial cells, as well as removal of any potential pathogens, debris and waste products. In patients with dry eye disease, the tear film is typically unstable or disrupted (for example, as a result of reduced aqueous secretion or increased evaporation of the tear film, or reduced secretion of mucin or lipids) and consequently, the corneal tissue, and conjunctiva may become less protected and vulnerable and/or prone to damage and deterioration.

The severity of ocular surface damage (which may be characterized by, for example punctate disruption of the corneal epithelium or surface disruption of the bulbar conjunctiva) may be assessed by corneal and conjunctival staining measurements, for example such as described herein, i.e. fluorescein staining (NEI scale) and lissamine green staining (Oxford scale), which highlight and stain in particular, dead or damaged corneal and conjunctival cells. Particularly, central corneal fluorescein staining (NEI scale), which assays the central corneal area (as compared to the peripheral corneal area including inferior, superior, nasal, and temporal regions of the cornea), reflects ocular surface damage that impacts visual function impairment.

As used herein, the term 'corneal staining' or 'total corneal staining', optionally in conjunction with the mention of fluorescein, or a dye that is suitable or adapted for staining of the cornea, refers to staining observed as a sum in respect of all regions of the cornea, i.e. the inferior, superior, central, temporal, and nasal regions of the cornea. The term 'central corneal staining' or the like (i.e. with specific corneal region prefacing) and optionally in conjunction with the dye used for staining, such as fluorescein, refers specifically to staining observed only in the specified anatomical region.

As used herein, the term 'conjunctival staining' or 'total conjunctival staining', optionally in conjunction with the mention of fluorescein or a dye suitable or adapted for staining of the cornea, refers to staining observed as a sum in respect of all regions of the conjunctiva, i.e. the temporal and nasal regions of the conjunctiva. Where the term is used specifying the specific conjunctival region (e.g. nasal conjunctiva staining), optionally in conjunction with mention of the dye used for staining, such as lissamine green, it is to be understood that this refers specifically to staining observed in said region.

In one embodiment, the pharmaceutical composition for use according to the invention may be used to treat ocular surface damage, such as corneal damage and/or conjunctival damage, in a subject suffering from dry eye disease, preferably said subject having a total corneal fluorescein staining score of at least equal to, or greater than 6 (≥6), the score being the sum of scores obtained for inferior, superior, central, nasal, and temporal regions of the cornea, based on the NEI grading scale of 0-3. In another embodiment, the pharmaceutical composition for use according to the invention may be used to treat ocular surface damage, such as corneal damage and/or conjunctival damage, in a subject suffering from dry eye disease, preferably said subject having a central corneal fluorescein staining score of at least equal to, or greater than 1 (≥1), based on the NEI grading scale of 0-3. In another embodiment, said subject may in addition also have a total lissamine green conjunctival staining score (sum of temporal and nasal regions), based on the Oxford scale, of at least equal to, or greater than 2 (i.e. ≥2).

In a preferred embodiment, the invention relates to a pharmaceutical composition for use in the treatment of ocular surface damage in a subject suffering from dry eye disease, wherein the composition comprises about 0.05 to 0.1% (w/v) cyclosporine dissolved in 1-perfluorobutyl-pentane, and optionally up to about 1.0% (w/w) of ethanol; and wherein the amount of cyclosporine administered in a single dose per eye is about 4 to 12 μg. In a specific embodiment, such use may be for the treatment of corneal damage.

In a further preferred embodiment, such pharmaceutical composition may be used in the treatment of ocular surface damage in a subject suffering from moderate to severe dry eye disease, preferably wherein the composition is administered twice daily, or wherein the total daily administered dose is less than about 28 μg per eye, or wherein preferably the daily administered dose does not exceed about 24 μg. Even more preferably, the total daily administered dose per eye is below about 20 μg, or below about 10 μg.

In another embodiment, the topically administered single dose per eye used in the treatment of ocular surface damage may be about 5 to 10 μg, or more preferably, about 5 μg or about 10 μg. In yet another embodiment, the topically administered single dose per eye used in the treatment of ocular surface damage, wherein the ocular surface damage is corneal damage, may be about 5 to 10 μg, or more preferably, about 5 μg or about 10 μg.

In yet a further preferred embodiment of the invention in respect of treatment of ocular surface damage in subjects suffering from dry eye disease, about 5 μg of cyclosporine is administered per single dose per eye, of a pharmaceutical composition comprising 0.05% (w/v) of cyclosporine dissolved in 1-perfluorobutyl-pentane, and optionally up to about 1.0% (w/w) ethanol.

In another preferred embodiment of the invention in respect of treatment of ocular surface damage in subjects suffering from dry eye disease, about 10 μg of cyclosporine is administered per single dose per eye, of a pharmaceutical composition comprising 0.1% (w/v) of cyclosporine dissolved in 1-perfluorobutyl-pentane, and optionally up to about 1.0% (w/w) ethanol.

In particular, it has been found that ocular surface damage such as corneal or conjunctival damage is effectively treated and reduced, as observed in patients undergoing treatment with the compositions as defined and as administered according to the invention (ref. FIGS. 2 and 3), as evidenced by a distinct reduction, compared to that observed in subjects prior to treatment, of corneal and conjunctival staining. Moreover, compared to the comparator product and the vehicle, an earlier onset of efficacy in the treatment of corneal damage was observed, i.e. already within two to four weeks of treatment time.

Preferably, the pharmaceutical compositions and dosages thereof as described herein may be used for the treatment of a subject with moderate to severe dry eye disease, optionally wherein the subject is not responsive to treatment with artificial tears.

The severity of dry eye disease in subjects or patients can be classified and scored using one or more, or a combination of standard tests. For example, the severity of dry eye disease may be determined using tests based on the assessment of patient perception of ocular symptoms and their effect on vision, based on questionnaires such as the Ocular Surface Disease Index (OSDI) questionnaire which is a 12-item question focused on symptoms of ocular irritation associated with dry eye disease and their impact on daily activities and lifestyle, or the dry eye symptom visual analogue scale (VAS), where subjects are asked to rate their ocular symptoms (both eyes simultaneously) due to ocular dryness by placing a vertical mark on the horizontal line to indicate the level of discomfort (0 corresponds to "no dryness" and 100% corresponds to "maximal dryness") and about the severity of dry eye symptoms, dryness, sticky feeling, burning/stinging, foreign body sensation, itching, blurred vision, sensitivity to light, and pain, as well as frequency in occurrence of dryness.

Dry eye disease may also be evaluated and determined using any combination of objective clinical measures such as the Schirmer test type 1, fluorescein staining and/or lissamine green staining of the cornea and conjunctiva, and tear-film break up time (TBUT) as a measurement of tear quality.

Within the context of the present invention, it is understood that any one of these measures of determining the severity of dry eye disease, or combination thereof may be applied.

Preferably, a subject or patient with moderate to severe dry eye, prior to treatment with the compositions defined herein, may have at least one or a combination of the following: a total corneal fluorescein staining score of ≥6 according to NEI grading (i.e. equal to or greater than 6 of the sum of scoring for the inferior, superior, central, nasal, and temporal cornea regions); being symptomatic (i.e. a score of ≥40 (equal to or greater than 40) on the dryness visual scale (VAS); or a score ≥20 on the Ocular Surface Disease Index (OSDI)); or a Schirmer's Test I score of between ≥2 mm and 8 mm (i.e. equal to or greater than 2 mm, but equal to or less than 8 mm);

In a further embodiment, the pharmaceutical compositions for use according to the invention may also be used for the treatment of subjects with dry eye disease who are not responsive to treatment with artificial tears.

Artificial tears, also known as lubricating eye drops or tear substitutes are used for relief and treatment of the symptoms of dry eye disease, and which normally may be obtained over the counter (OTC). These are normally aqueous-based compositions, in the form of solutions, but also in the form of gels or ointments which function by adding moisture to the eyes, and usually may comprise lubricating agents (e.g. hydroxypropyl methyl cellulose (HPMC), carbomethylcellulose (CMC), polyvinyl alcohol, liquid polyols such as propylene glycol, polyethylene glycol) and may contain additives which promote healing (e.g. hyaluronic acid) or mimic electrolyte composition of natural tear film, or which promote retention (e.g. gelling agents such as carbomers) of the composition on the eye surface.

Preferably, the pharmaceutical compositions for use according to the invention may be used to treat subjects suffering from dry eye disease, in particular subjects with moderate to severe dry eye disease, with persisting dry eye disease symptoms, and associated conditions even following a treatment period with only artificial tears over a period of at least 2 weeks, or at least 1 month, or at least about 6 months.

A dose of a composition for use according to the present invention and as described in any one of the embodiments herein is preferably topically administered in the form of a (i.e. one) single drop to an eye of a subject. The drop may be administered to the surface of the eye, preferably to any surface region or tissue of the eye that is accessible to topical administration or instillation, for example to the cornea or conjunctiva. The single drop of the composition may be instilled directly onto a surface of the eye, such as the corneal surface of the eye, or alternatively into a space i.e. sac or pocket formed by gently pulling down of the lower eyelid of an eye. As used herein, the term 'administration to an eye' or 'per eye' refers to the administration of a given dose, e.g. a single dose, of a pharmaceutical composition according to the invention to an individual eye of a subject. The therapy of the dry eye disease and dry eye disease associated conditions as described herein however, should be understood as being not limited to the treatment of a single eye in a subject, but as being also inclusive of a therapy involving the administration of compositions according to the present invention to each i.e. both eyes of a subject which are affected by the dry eye condition.

Preferably, the pharmaceutical compositions for any of the uses described herein are administered at a dose of a single drop four times a day per eye. In a more preferred embodiment, the compositions are administered to the eye as a single drop twice per day per eye. Thus, a patient undergoing treatment for both eyes in accordance with such dosing scheme would receive a total of two drops for each eye on each day of a given treatment period.

Where the pharmaceutical composition is administered more than once per day to each eye, for example four times daily, or two times daily per eye it is preferred, in a further embodiment, that the time interval between topical administration of the composition to the eye or eye surface is at least 4 hours, or at least 6 hours, or at least 12 hours.

In a further embodiment, the pharmaceutical compositions for use according to the invention are administered over a treatment period of at least 1 month (four weeks), and more preferably at least 4 months (16 weeks). In another embodiment, the pharmaceutical compositions for use in the treatment of the dry eye disease conditions and disorders as described herein may be administered on a continuous basis while dry eye disease symptoms and indicators persist.

Preferably, the pharmaceutical compositions for use in accordance with the invention may comprise up to about 1.0% (w/w) of ethanol.

As used herein, the term "up to about" or "up to" used in context of a parameter, such as presently in relation to the amount of ethanol in the composition, refers to any value of the parameter greater than zero and up to, and inclusive of, the defined parameter. For example, an amount of "up to about 1.0% (w/w) of ethanol" should be understood as including any value greater than zero ranging up to and including the value of 1.0% (w/w) of ethanol, and would include, for example, values such as 0.01%, 0.05%, 0.1%, 0.2%, 0.3%, 0.4%, 0.5% 0.6%, 0.7, 0.8, 0.9, 0.95%, 0.99% (w/w) of ethanol, taking into account any degree of variability usually observed in measuring or determining this parameter, using the standard techniques and equipment known in the relevant field.

In one embodiment of the invention, the compositions for the therapeutic uses as described herein may consist essentially of about 0.05% or 0.1% (w/v) cyclosporine dissolved in 1-perfluorobutyl-pentane, and optionally about 1.0% (w/w) of ethanol.

In another embodiment, the compositions as described herein are essentially free of ethanol, in which the composition consists essentially only of cyclosporine in an amount as described in any of the embodiments described herein dissolved in 1-perfluorobutyl-pentane.

The absence of an organic co-solvent such as ethanol may offer the advantages of a simpler two component formulation compared to a three component formulation additionally comprising a co-solvent such as ethanol. The further inclusion, of even one additional composition component may add complexity in terms of factors such as cost, manufacturing, handling, packaging, and also patient compliance.

In preferred embodiments of the invention, the compositions for use as described herein may preferably comprise, or consist of:

- 0.05 to 0.1% (w/v) of cyclosporine dissolved in 1-perfluorobutyl-pentane and 0.5% (w/w) ethanol, or
- 0.05 to 0.1% (w/v) of cyclosporine dissolved in 1-perfluorobutyl-pentane and 1.0% (w/w) ethanol, or
- 0.05% (w/v) cyclosporine dissolved in 1-perfluorobutyl-pentane and 0.5% (w/w) ethanol, or
- 0.1% (w/v) of cyclosporine dissolved in 1-perfluorobutyl-pentane and 0.5% (w/w) ethanol, or
- 0.1% (w/v) cyclosporine dissolved in 1-perfluorobutyl-pentane and 1.0% (w/w) ethanol, or
- 0.05% (w/v) cyclosporine dissolved in 1-perfluorobutyl-pentane and 1.0% (w/w) ethanol, or
- 0.05 to 0.1% (w/v) of cyclosporine dissolved in 1-perfluorobutyl-pentane, or
- 0.1% (w/v) cyclosporine dissolved in 1-perfluorobutyl-pentane, or
- 0.05% (w/v) cyclosporine dissolved in 1-perfluorobutyl-pentane.

The compositions of the invention are preferably provided as a clear solution, wherein the cyclosporine is fully dissolved and in solution in the 1-perfluorobutyl-pentane (at room temperature conditions i.e. between 15 to 25° C.). If ethanol is included, said compositions are also provided as a clear solution of cyclosporine dissolved and in solution in 1-perfluorobutyl-pentane and the ethanol. In a preferred embodiment, the compositions are provided in sterile form.

In another preferred embodiment, the pharmaceutical compositions for use according to the present invention are substantially free of water and/or substantially free of a preservative. As understood herein, the term 'substantially free', or alternatively 'essentially free' in reference to a composition constituent refers to the presence of said constituent in no more than trace amounts and that if present in trace amounts the constituent provides no technical contribution to the composition.

Preferably, the pharmaceutical compositions for use according to the present invention are substantially free of water, substantially free of a preservative and are effective in inhibiting microbial growth.

In another preferred embodiment, the pharmaceutical compositions for use according to the present invention are characterized by a remarkable wetting and spreading behaviour by which they can rapidly and effectively spread over the surface of the eye, such as the corneal and/or the conjunctival surface. Thus, a droplet (drop) of the pharmaceutical compositions for use according to the present invention when administered to the surface of the eye leads to rapid spreading of the compositions over the corneal and/or the conjunctival surface.

Preferably, the pharmaceutical compositions for use according to the present invention form small droplets (drops), in the range of about 8-12 μl, more preferably about 9-11 μl, most preferably about 10 μl, when administered from a drop dispenser. This distinguishes the compositions of the present invention from the 0.05% cyclosporine aqueous (o/w) emulsions, that are characterized by droplet sizes of about 28.5 μl.

In another preferred embodiment, the pharmaceutical compositions for use according to the present invention are characterized by the comparable low amount of cyclosporine administered in a single dose per eye, such as about 4-12 μg of cyclosporine, preferably 5-10 μg cyclosporine administered in a single dose per eye. This distinguishes the compositions of the present invention from the 0.05% cyclosporine aqueous (o/w) emulsions, that are characterized by droplet sizes of about 28.5 μl and allows for reduction of about 30 to 65% of the total daily dose when utilizing the pharmaceutical compositions for use according to the present invention.

As used herein, the term "consists" and related terms "consisting" or "consist" is to be understood as meaning that no other features, other than those prefaced by the term are present. In the context of pharmaceutical compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of").

The use of a pharmaceutical composition as described in any one of the above embodiments in the manufacture or preparation of a medicament or a medicine for the treatment of a subject in need thereof in relation to any one of preferred dry eye disease conditions described herein are also provided for in the context of the present invention. Further provided for within the context of the present invention, are also methods of treating subjects diagnosed with, and/or suffering from said dry eye disease conditions as described herein, wherein the methods may comprise the topical administration, such as by direct topical instillation to the eye, of any one of the defined compositions, preferably in any one of the described doses or amounts, and/or over any one of the defined periods for therapy.

Said treatment methods and compositions for therapeutic use are moreover preferably targeted towards human subjects diagnosed and/or suffering dry eye disease.

In yet a further aspect, the invention provides also a kit comprising a pharmaceutical composition for use according to the invention and any of the embodiments described above, wherein the kit comprises a container for holding the pharmaceutical composition and a drop dispenser adapted for administering about 8 to 12 μl volume of the composition per drop.

In a further embodiment, the drop dispenser is adapted for administering about 10 μl of the composition per drop.

As understood herein, the drop dispenser may be a dispenser or applicator means which may be mounted, fixed or connected to the container for holding the pharmaceutical composition. Preferably, the drop dispenser is adapted for dispensing a single dose in the form of a single drop of the composition. More preferably, the drop dispenser is adapted for dispensing a single dose of 8- to 12-μl volume, or is adapted for dispensing a single dose of about 10-μl volume.

The container for holding the pharmaceutical composition as understood herein is preferably of a volume which may hold a single dose, but more preferably of a volume which may hold multiple or a plurality of doses of the composition. In an embodiment of the invention, the container of the kit may hold up to 160 doses of the pharmaceutical composition for use according to the present invention.

The container and/or the drop dispenser preferably may be manufactured from a thermoplastic material or polymer. In a one embodiment, the container and/or drop dispenser is manufactured from a thermoplastic material selected from polyethylene and polypropylene.

In one particular embodiment, the drop dispenser is manufactured from a polyethylene material, preferably selected from low density polyethylene and high density polyethylene, and more preferably is manufactured from a high-density polyethylene. In another embodiment, the container is manufactured from a polypropylene or polyethylene material, and more preferably is manufactured from polypropylene.

In yet a further embodiment, the invention relates to a kit comprising a pharmaceutical composition for use according to the invention, the kit comprising a container for holding the pharmaceutical composition and a drop dispenser adapted for administering about 8 to 12 μl per drop wherein the container is manufactured from polypropylene and wherein the drop dispenser is manufactured from a polyethylene selected from a low density polyethylene and a high density polyethylene, preferably a high density polyethylene.

Preferably, the container has a volume, or an interior space which is at least partially filled with a pharmaceutical composition for use according to the invention. In a further embodiment, the ratio of the volume of the pharmaceutical composition in the container to the total volume of the container is between 0.4 and 0.7. The total volume of the container, as understood herein refers to the total interior volume formed by the interior dimensions of the container. The volume of the pharmaceutical composition in the container refers to the fill volume, i.e. the volume of the pharmaceutical composition held in the container. For example, in a kit comprising a container with a total volume of 3.0 mL, it is preferred that the container holds a volume of 2.0 mL of a pharmaceutical composition according to the invention. Here, the ratio of the volume of the pharmaceutical composition in the container to the total volume of the container would be about 0.7.

Particularly preferred are kits comprising a pharmaceutical composition for use in accordance with the present invention, wherein the kit comprises, in addition to a drop dispenser adapted for administering about 8 to 12 μl per drop, any one of the following:

- about 2.0 mL of the pharmaceutical composition filled in a 3.0 mL volume container (i.e. a respective ratio of about 0.7); or
- about 2.0 mL of a pharmaceutical composition filled in a 5.0 mL volume container (i.e. a respective ratio of about 0.4); or
- about 2.5 mL of a pharmaceutical composition filled in a 5.0 mL volume container (i.e. a respective ratio of about 0.5).

Also preferred is a kit comprising a pharmaceutical composition for use in accordance with the present invention, wherein the kit comprises a container for holding the pharmaceutical composition and a drop dispenser adapted for administering about 8 to 12 μl per drop and wherein the ratio of the volume of head space in the container to the volume of the pharmaceutical composition is between 0.5 to 1.5. As understood herein, the volume of head space (or head space volume) in the container refers to the interior volume of the container, formed by the interior dimensions of the container which is not filled or occupied by the liquid pharmaceutical composition but which may contain atmosphere or inert gas.

For example, in a kit comprising a container holding a fill volume of 2.5 mL of a pharmaceutical composition for use according to the present invention, it is preferred that the head space volume available in the container is about 2.5 mL, wherein the ratio of the head space to pharmaceutical composition fill volume is about 1.0.

Particularly preferred are kits comprising a pharmaceutical composition for use in accordance with the present invention, wherein the kit comprises, in addition to a drop dispenser adapted for administering about 8 to 12 μl per drop, or preferably about 10 μl per drop, any one of the following:

- a container holding about 2.0 mL of the pharmaceutical composition, wherein the container has about 1.0 mL volume of head space (i.e. a head space to fill volume ratio of about 0.5); or
- a container holding about 2.0 mL of the pharmaceutical composition, wherein the container has about 3.0 mL volume of head space (i.e. a head space to fill volume ratio of about 1.5); or
- a container holding about 2.4 mL of the pharmaceutical composition, wherein the container has about 2.6 mL volume of head space (i.e. a head space to fill volume ratio of about 1.1).

Such kits as provided in accordance with these embodiments may improve storage and dispensability (i.e., ease and consistency in dispensing) of the pharmaceutical compositions.

Further, the present invention comprises the following items 1 to 37, relating to a method for treating dry eye disease:

1. A method of treating dry eye disease, the method comprising topically administering twice daily to an eye of a human with dry eye disease a composition comprising about 0.05 to 0.1% (w/v) cyclosporine dissolved in 1-perfluorobutyl-pentane, wherein the amount of cyclosporine administered in a single dose per eye is about 4 to 12 μg cyclosporine, and wherein said method is therapeutically effective in treating dry eye in said human.
2. A method of treating dry eye disease according to Item 1, wherein said composition further comprises up to about 1% (w/w) ethanol.
3. A method of treating dry eye disease according to Item 1, wherein said composition consists of cyclosporine dissolved in a solution of about 99% (w/w) 1-perfluorobutyl-pentane and about 1% (w/w) ethanol.

4. A method of treating dry eye disease according to Item 1, wherein said composition consists of cyclosporine dissolved in a solution of at about least 99% (w/w) 1-perfluorobutyl-pentane and up to about 1% (w/w) ethanol.
5. A method of treating dry eye disease according to Item 1, wherein said composition further comprises up to about 0.5% (w/w) ethanol.
6. A method of treating dry eye disease according to Item 1, wherein said composition consists of cyclosporine dissolved in a solution of about 99.5% (w/w) 1-perfluorobutyl-pentane and about 0.5% (w/w) ethanol.
7. A method of treating dry eye disease according to Item 1, wherein said composition consists of the cyclosporine dissolved in a solution of at least about 99.5% (w/w) 1-perfluorobutyl-pentane and up to about 0.5% (w/w) ethanol.
8. A method of treating dry eye disease, the method comprising topically administering twice daily to an eye of a human with dry eye disease a composition comprising about 0.05% (w/v) cyclosporine dissolved in 1-perfluorobutyl-pentane, wherein said composition is substantially free of water and is substantially free of a preservative, wherein the amount of cyclosporine administered in a single dose per eye is about 5 µg cyclosporine, and wherein said method is therapeutically effective in treating dry eye in said human.
9. A method of treating dry eye disease according to Item 8, wherein said composition further comprises up to about 1% (w/w) ethanol.
10. A method of treating dry eye disease according to Item 8, wherein said composition consists of the cyclosporine dissolved in a solution of about 99% (w/w) 1-perfluorobutyl-pentane and about 1% (w/w) ethanol.
11. A method of treating dry eye disease according to Item 8, wherein said composition consists of the cyclosporine dissolved in a solution of at least about 99% (w/w) 1-perfluorobutyl-pentane and up to about 1% (w/w) ethanol.
12. A method of treating dry eye disease according to Item 8, wherein said composition further comprises up to about 0.5% (w/w) ethanol.
13. A method of treating dry eye disease according to Item 8, wherein said composition consists of the cyclosporine dissolved in a solution of about 99.5% (w/w) 1-perfluorobutyl-pentane and about 0.5% (w/w) ethanol.
14. A method of treating dry eye disease according to Item 8, wherein said composition consists of the cyclosporine dissolved in a solution of at least about 99.5% (w/w) 1-perfluorobutyl-pentane and up to about 0.5% (w/w) ethanol.
15. A method of treating dry eye disease according to any of the Items 8 to 14, wherein a reduction in corneal staining is achieved.
16. A method of treating dry eye disease according to Item 15, wherein a reduction in corneal staining is achieved over a four month treatment period.
17. A method of treating dry eye disease according to any of the Items 8 to 14, wherein a reduction in central corneal staining, and/or any one or combination of inferior, superior, nasal, or temporal corneal staining is achieved.
18. A method of treating dry eye disease according to any of the items 8 to 14, wherein an early onset of action is achieved.
19. A method of treating dry eye disease according to Item 18, wherein said early onset of action is measured by reduction in corneal and conjunctival staining and is achieved in about 2 to 4 weeks.
20. A method of treating dry eye disease according to any of the items 8 to 14, wherein visual impairment associated with dry eye disease is reduced.
21. A method of treating dry eye disease according to any of the items 8 to 14, wherein ocular surface damage associated with dry eye disease is reduced.
22. A method of treating dry eye disease according to any of the items 8 to 14, wherein said composition is safe, well tolerated and comfortable to the eye of the human.
23. A method of treating dry eye disease, the method comprising topically administering twice daily to an eye of a human with dry eye disease a composition comprising about 0.1% (w/v) cyclosporine dissolved in 1-perfluorobutyl-pentane, wherein said composition is substantially free of water and is substantially free of a preservative, wherein the amount of cyclosporine administered in a single dose per eye is about 10 µg cyclosporine, and wherein said method is therapeutically effective in treating dry eye in said human.
24. A method of treating dry eye disease according to Item 23, wherein said composition further comprises up to about 1% (w/w) ethanol.
25. A method of treating dry eye disease according to Item 23, wherein said composition consists of the cyclosporine dissolved in a solution of about 99% (w/w) 1-perfluorobutyl-pentane and about 1% (w/w) ethanol.
26. A method of treating dry eye disease according to Item 23, wherein said composition consists of cyclosporine dissolved in a solution of at least about 99% (w/w) 1-perfluorobutyl-pentane and up to about 1% (w/w) ethanol.
27. A method of treating dry eye disease according to Item 23, wherein said composition further comprises up to about 0.5% (w/w) ethanol.
28. A method of treating dry eye disease according to Item 23, wherein said composition consists of the cyclosporine dissolved in a solution of about 99.5% (w/w) 1-perfluorobutyl-pentane and about 0.5% (w/w) ethanol.
29. A method of treating dry eye disease according to Item 23, wherein said composition consists of the cyclosporine dissolved in a solution of at least about 99.5% (w/w) 1-perfluorobutyl-pentane and up to about 0.5% (w/w) ethanol.
30. A method of treating dry eye disease according to any of the items 23 to 29, wherein a reduction in corneal staining is achieved.
31. A method of treating dry eye disease according to Item 30, wherein a reduction in corneal staining is achieved over a four month treatment period.
32. A method of treating dry eye disease according to any of the items 23 to 29, wherein a reduction in central corneal staining and/or any one or combination of inferior, superior, nasal, or temporal corneal staining is achieved.
33. A method of treating dry eye disease according to any of the items 23 to 29 wherein an early onset of action is achieved.

34. A method of treating dry eye disease according to Item 33, wherein said early onset of action is measured by reduction in corneal and conjunctival staining and is achieved in about 2 to 4 weeks.
35. A method of treating dry eye disease according to any of the items 23 to 29, wherein visual impairment associated with dry eye disease is reduced.
36. A method of treating dry eye disease according to any of the items 23 to 29, wherein ocular surface damage associated with dry eye disease is reduced.
37. A method of treating dry eye disease according to any of the items 23 to 29, wherein said composition is safe, well tolerated and comfortable to the eye of the human.

Further, the present invention comprises the following items 38 to 72 relating to a method for reducing reading impairment associated with dry eye disease:

38. A method of reducing reading impairment associated with dry eye disease, the method comprising topically administering twice daily to an eye of a human with dry eye disease a composition comprising about 0.05 to 0.1% (w/v) cyclosporine dissolved in 1-perfluorobutyl-pentane, wherein the amount of cyclosporine administered in a single dose per eye is about 4 to 12 μg cyclosporine, and wherein said method is effective in reducing reading impairment in said human.
39. A method of reducing reading impairment according to Item 38, wherein said composition further comprises up to about 1% (w/w) ethanol.
40. A method of reducing reading impairment according to Item 38, wherein said composition consists of the cyclosporine dissolved in a solution of about 99% (w/w) 1-perfluorobutyl-pentane and about 1% (w/w) ethanol.
41. A method of reducing reading impairment according to Item 38, wherein said composition consists of the cyclosporine dissolved in a solution of at least about 99% (w/w) 1-perfluorobutyl-pentane and up to about 1% (w/w) ethanol.
42. A method of reducing reading impairment according to Item 38, wherein said composition further comprises up to about 0.5% (w/w) ethanol.
43. A method of reducing reading impairment according to Item 38, wherein said composition consists of the cyclosporine dissolved in a solution of about 99.5% (w/w) 1-perfluorobutyl-pentane and about 0.5% (w/w) ethanol.
44. A method of reducing reading impairment according to Item 38, wherein said composition consists of the cyclosporine dissolved in a solution of at least about 99.5% (w/w) 1-perfluorobutyl-pentane and up to about 0.5% (w/w) ethanol.
45. A method of reducing reading impairment associated with dry eye disease, the method comprising topically administering twice daily to an eye of a human with dry eye disease a composition comprising about 0.05% (w/v) cyclosporine dissolved in 1-perfluorobutyl-pentane, wherein said composition is substantially free of water and is substantially free of a preservative, wherein the amount of cyclosporine administered in a single dose per eye is about 5 μg cyclosporine, and wherein said method is effective in reducing reading impairment in said human.
46. A method of reducing reading impairment according to Item 45, wherein said composition further comprises up to about 1% (w/w) ethanol.
47. A method of reducing reading impairment according to Item 45 wherein said composition consists of the cyclosporine dissolved in a solution of about 99% (w/w) 1-perfluorobutyl-pentane and about 1% (w/w) ethanol.
48. A method of reducing reading impairment according to Item 45 wherein said composition consists of the cyclosporine dissolved in a solution of at least about 99% (w/w) 1-perfluorobutyl-pentane and up to about 1% (w/w) ethanol.
49. A method of reducing reading impairment according to Item 45, wherein said composition further comprises up to about 0.5% (w/w) ethanol.
50. A method of reducing reading impairment according to Item 45, wherein said composition consists of the cyclosporine dissolved in a solution of about 99.5% (w/w) 1-perfluorobutyl-pentane and about 0.5% (w/w) ethanol.
51. A method of reducing reading impairment according to Item 45, wherein said composition consists of the cyclosporine dissolved in a solution at least about 99.5% (w/w) 1-perfluorobutyl-pentane and up to about 0.5% (w/w) ethanol.
52. A method of reducing reading impairment according to any of the items 45 to 51, wherein a reduction in corneal staining is achieved.
53. A method of reducing reading impairment according to Item 52, wherein a reduction in corneal staining is achieved over a four month treatment period.
54. A method of reducing reading impairment according to any of the items 45 to 51, wherein a reduction in central corneal staining and/or any one or combination of inferior, superior, nasal, or temporal corneal staining is achieved.
55. A method of reducing reading impairment according to any of the items 45 to 51, wherein an early onset of action is achieved.
56. A method of reducing reading impairment according to Item 55, wherein said early onset of action is measured by reduction in corneal and conjunctival staining and is achieved in about 2 to 4 weeks.
57. A method of reducing reading impairment according to any of the items 45 to 51, wherein ocular surface damage associated with dry eye disease is reduced.
58. A method of reducing reading impairment according to any of the items 45 to 51, wherein said composition is safe, well tolerated and comfortable to the eye of the human.
59. A method of reducing reading impairment associated with dry eye disease, the method comprising topically administering twice daily to an eye of a human with dry eye disease a composition comprising about 0.1% (w/v) cyclosporine dissolved in 1-perfluorobutyl-pentane, wherein said composition is substantially free of water and is substantially free of a preservative, wherein the amount of cyclosporine administered in a single dose per eye is about 10 μg cyclosporine, and wherein said method is effective in reducing reading impairment in said human.
60. A method of reducing reading impairment according to Item 59, wherein said composition further comprises up to about 1% (w/w) ethanol.
61. A method of reducing reading impairment according to Item 59, wherein said composition consists of the cyclosporine dissolved in a solution of about 99% (w/w) 1-perfluorobutyl-pentane and about 1% (w/w) ethanol.
62. A method of reducing reading impairment according to Item 59, wherein said composition consists of cyclosporine dissolved in a solution of at least about 99% (w/w) 1-perfluorobutyl-pentane and up to about 1% (w/w) ethanol.

63. A method of reducing reading impairment according to Item 59, wherein said composition further comprises up to about 0.5% (w/w) ethanol.

64. A method of reducing reading impairment according to Item 59, wherein said composition consists of the cyclosporine dissolved in a solution of about 99.5% (w/w) 1-perfluorobutyl-pentane and about 0.5% (w/w) ethanol.

65. A method of reducing reading impairment according to Item 59, wherein said composition consists of the cyclosporine dissolved in a solution of at least about 99.5% (w/w) 1-perfluorobutyl-pentane and up to about 0.5% (w/w) ethanol.

66. A method of reducing reading impairment according to any of the items 59 to 65, wherein a reduction in corneal staining is achieved.

67. A method of reducing reading impairment according to Item 66, wherein a reduction in corneal staining is achieved over a four month treatment period.

68. A method of reducing reading impairment according to any of the items 59 to 65, wherein a reduction in central corneal staining and/or any one or combination of inferior, superior, nasal, or temporal corneal staining is achieved.

69. A method of reducing reading impairment according to any of the items 59 to 65, wherein an early onset of action is achieved.

70. A method of reducing reading impairment according to Item 69, wherein said early onset of action is measured by reduction in corneal staining and is achieved in about 2 to 4 weeks.

71. A method of reducing reading impairment according to any of the items 459 to 65 or items 59 to 65, wherein ocular surface damage associated with dry eye disease is reduced.

72. A method of reducing reading impairment according to any of the items 59 to 65, wherein said composition is safe, well tolerated and comfortable to the eye of the human.

Further, the present invention comprises the following items 73 to 107 relating to a method of reducing ocular surface damage associated with dry eye disease:

73. A method of reducing ocular surface damage associated with dry eye disease, the method comprising topically administering twice daily to an eye of a human with dry eye disease a composition comprising about 0.05 to 0.1% (w/v) cyclosporine dissolved in 1-perfluorobutyl-pentane, wherein the amount of cyclosporine administered in a single dose per eye is about 4 to 12 μg cyclosporine, and wherein said method is effective in reducing ocular surface damage in said human.

74. A method of reducing ocular surface damage according to Item 73, wherein said composition further comprises up to about 1% (w/w) ethanol.

75. A method of reducing ocular surface damage according to Item 73, wherein said composition consists of the cyclosporine dissolved in a solution of about 99% (w/w) 1-perfluorobutyl-pentane and about 1% (w/w) ethanol.

76. A method of reducing ocular surface damage according to Item 73, wherein said composition consists of the cyclosporine dissolved in a solution of at least about 99% (w/w) 1-perfluorobutyl-pentane and up to about 1% (w/w) ethanol.

77. A method of reducing ocular surface damage according to Item 73, wherein said composition further comprises up to about 0.5% (w/w) ethanol.

78. A method of reducing ocular surface damage according to Item 73, wherein said composition consists of the cyclosporine dissolved in a solution of about 99.5% (w/w) 1-perfluorobutyl-pentane and about 0.5% (w/w) ethanol.

79. A method of reducing ocular surface damage according to Item 73, wherein said composition consists of the cyclosporine dissolved in a solution of at least about 99.5% (w/w) 1-perfluorobutyl-pentane and up to about 0.5% (w/w) ethanol.

80. A method of reducing ocular surface damage associated with dry eye disease, the method comprising topically administering twice daily to an eye of a human with dry eye disease a composition comprising about 0.05% (w/v) cyclosporine dissolved in 1-perfluorobutyl-pentane, wherein said composition is substantially free of water and is substantially free of a preservative, wherein the amount of cyclosporine administered in a single dose per eye is about 5 μg cyclosporine, and wherein said method is effective in reducing ocular surface damage in said human.

81. A method of reducing ocular surface damage according to Item 80, wherein said composition further comprises up to about 1% (w/w) ethanol.

82. A method of reducing ocular surface damage according to Item 80, wherein said composition consists of the cyclosporine dissolved in a solution of about 99% (w/w) 1-perfluorobutyl-pentane and about 1% (w/w) ethanol.

83. A method of reducing ocular surface damage according to Item 80, wherein said composition consists of the cyclosporine dissolved in a solution of at least about 99% (w/w) 1-perfluorobutyl-pentane and up to about 1% (w/w) ethanol.

84. A method of reducing ocular surface damage according to Item 80, wherein said composition further comprises up to about 0.5% (w/w) ethanol.

85. A method of reducing ocular surface damage according to Item 80, wherein said composition consists of the cyclosporine dissolved in a solution of about 99.5% (w/w) 1-perfluorobutyl-pentane and about 0.5% (w/w) ethanol.

86. A method of reducing ocular surface damage according to Item 80, wherein said composition consists of the cyclosporine dissolved in a solution of at least about 99.5% (w/w) 1-perfluorobutyl-pentane and up to about 0.5% (w/w) ethanol.

87. A method of reducing ocular surface damage according to any of the items 80 to 86, wherein a reduction in corneal staining is achieved.

88. A method of reducing ocular surface damage according to Item 87, wherein a reduction in corneal staining is achieved over a four month treatment period.

89. A method of reducing ocular surface damage according to any of the items 80 to 86, wherein a reduction in central corneal staining and/or any one or combination of inferior, superior, nasal, or temporal corneal staining is achieved.

90. A method of reducing ocular surface damage according to any of the items 80 to 86, wherein an early onset of action is achieved.

91. A method of reducing ocular surface damage according to Item 90, wherein said early onset of action is measured by reduction in corneal and conjunctival staining and is achieved in about 2 to 4 weeks.
92. A method of reducing ocular surface damage according to any of the items 80 to 86, wherein visual impairment associated with dry eye disease is reduced.
93. A method of reducing ocular surface damage according to any of the items 80 to 86, wherein said composition is safe, well tolerated and comfortable to the eye of the human.
94. A method of reducing ocular surface damage associated with dry eye disease, the method comprising topically administering twice daily to an eye of a human with dry eye disease a composition comprising about 0.1% (w/v) cyclosporine dissolved in 1-perfluorobutyl-pentane, wherein said composition is substantially free of water and is substantially free of a preservative, wherein the amount of cyclosporine administered in a single dose per eye is about 10 μg cyclosporine, and wherein said method is effective in reducing ocular surface damage in said human.
95. A method of reducing ocular surface damage according to Item 94, wherein said composition further comprises up to about 1% (w/w) ethanol.
96. A method of reducing ocular surface damage according to Item 94, wherein said composition consists of the cyclosporine dissolved in a solution of about 99% (w/w) 1-perfluorobutyl-pentane and about 1% (w/w) ethanol.
97. A method of reducing ocular surface damage according to Item 94, wherein said composition consists of the cyclosporine dissolved in a solution of at least about 99% (w/w) 1-perfluorobutyl-pentane and up to about 1% (w/w) ethanol.
98. A method of reducing ocular surface damage according to Item 94, wherein said composition further comprises up to about 0.5% (w/w) ethanol.
99. A method of reducing ocular surface damage according to Item 94 wherein said composition consists of the cyclosporine dissolved in a solution of about 99.5% (w/w) 1-perfluorobutyl-pentane and about 0.5% (w/w) ethanol.
100. A method of reducing ocular surface damage according to Item 94 wherein said composition consists of the cyclosporine dissolved in a solution of at least about 99.5% (w/w) 1-perfluorobutyl-pentane and up to about 0.5% (w/w) ethanol.
101. A method of reducing ocular surface damage according to any of the items 94 to 100, wherein a reduction in corneal staining is achieved.
102. A method of reducing ocular surface damage according to Item 101, wherein a reduction in corneal staining is achieved over a four month treatment period.
103. A method of reducing ocular surface damage according to any of the items 94 to 100 wherein a reduction in central corneal staining and/or any one or combination of inferior, superior, nasal, or temporal corneal staining is achieved.
104. A method of reducing ocular surface damage according to any of the items 94 to 100, wherein an early onset of action is achieved.
105. A method of reducing ocular surface damage according to Item 104, wherein said early onset of action is measured by reduction in corneal staining and is achieved in about 2 to 4 weeks.
106. A method of reducing ocular surface damage according to any of the items 94 to 100, wherein visual impairment associated with dry eye disease is reduced.
107. A method of reducing ocular surface damage according to any of the items 94 to 100, wherein said composition is safe, well tolerated and comfortable to the eye of the human.

Further, the present invention comprises the following items 108 to 140, relating to a method of reducing the total daily amount of cyclosporine administered topically to a human for the treatment of dry eye disease:

108. A method of reducing the total daily amount of cyclosporine administered topically to a human for the treatment of dry eye disease, the method comprising topically administering twice daily to an eye of said human a single drop per eye of a composition comprising about 0.05 to 0.1% (w/v) cyclosporine dissolved in 1-perfluorobutyl-pentane, wherein the amount of cyclosporine administered in a single dose per eye is about 4 to 12 μg cyclosporine and wherein said method reduces the amount of cyclosporine per total daily dose by about 30 to 65% and is at least as therapeutically effective in treating dry eye as compared to twice daily topical administration of a single drop per eye of a 0.05% (w/v) cyclosporine aqueous (o/w) emulsion; or
    wherein the amount of cyclosporine administered in a single dose per eye is about 5 to 10 μg cyclosporine and wherein said method reduces the amount of cyclosporine per total daily dose by about 30 to 65% and is at least as therapeutically effective in treating dry eye as compared to twice daily topical administration of a single drop per eye of a 0.05% (w/v) cyclosporine aqueous (o/w) emulsion.
109. A method of reducing the total daily amount of cyclosporine administered topically to a human for the treatment of dry eye disease according to Item 108, wherein said composition further comprises up to about 1% (w/w) ethanol.
110. A method of reducing the total daily amount of cyclosporine administered topically to a human for the treatment of dry eye disease according to Item 108, wherein said composition consists of the cyclosporine dissolved in a solution of about 99% (w/w) 1-perfluorobutyl-pentane and about 1% (w/w) ethanol.
111. A method of reducing the total daily amount of cyclosporine administered topically to a human for the treatment of dry eye disease according to Item 108, wherein said composition consists of the cyclosporine dissolved in a solution of at least about 99% (w/w) 1-perfluorobutyl-pentane and up to about 1% (w/w) ethanol.
112. A method of reducing the total daily amount of cyclosporine administered topically to a human for the treatment of dry eye disease according to Item 108, wherein said composition further comprises up to about 0.5% (w/w) ethanol.
113. A method of reducing the total daily amount of cyclosporine administered topically to a human for the treatment of dry eye disease according to Item 108, wherein said composition consists of the cyclosporine dissolved in a solution of about 99.5% (w/w) 1-perfluorobutyl-pentane and about 0.5% (w/w) ethanol.
114. A method of reducing the total daily amount of cyclosporine administered topically to a human for the treatment of dry eye disease according to Item 108, wherein said composition consists of the cyclosporine dissolved in a solution of at least about 99.5% (w/w) 1-perfluorobutyl-pentane and up to about 0.5% (w/w) ethanol.

115. A method of reducing the total daily amount of cyclosporine administered topically to a human for the treatment of dry eye disease according to Item 108 to 114, wherein the single drop of said composition has a drop volume of about 10 μl and the single drop of said emulsion has a drop volume of about 28.5 μl.

116. A method of reducing the total daily amount of cyclosporine administered topically to a human for the treatment of dry eye disease according to Item 108 to 114, wherein the systemic exposure to cyclosporine is reduced as compared to twice daily topical administration of a single drop of a 0.05% (w/v) cyclosporine aqueous (o/w) emulsion.

117. A method of reducing the total daily amount of cyclosporine administered topically to a human for the treatment of dry eye disease according to Item 108 to 114, wherein one or more adverse effects are reduced as compared to twice daily topical administration of a single drop of a 0.05% (w/v) cyclosporine aqueous (o/w) emulsion.

118. A method of reducing the total daily amount of cyclosporine administered topically to a human for the treatment of dry eye disease according to Item 117, wherein the adverse effects are selected from the group consisting of visual blurring, eye pain, and eye irritation.

119. A method of reducing the total daily amount of cyclosporine administered topically to a human for treatment of dry eye disease, the method comprising topically administering twice daily to an eye of a human with dry eye disease a single drop of a composition comprising about 0.05% (w/v) cyclosporine dissolved in 1-perfluorobutyl-pentane, wherein said composition is substantially free of water and is substantially free of a preservative, wherein the amount of cyclosporine administered in a single dose per eye is about 5 μg cyclosporine, and wherein said method reduces the amount of cyclosporine per total daily dose by about 65% and is at least as therapeutically effective in treating dry eye as compared to twice daily topical administration of a single drop per eye of a 0.05% (w/v) cyclosporine aqueous (o/w) emulsion.

120. A method of reducing the total daily amount of cyclosporine administered topically to a human for the treatment of dry eye disease according to Item 119, wherein said composition further comprises up to about 1% (w/w) ethanol.

121. A method of reducing the total daily amount of cyclosporine administered topically to a human for the treatment of dry eye disease according to Item 119, wherein said composition consists of the cyclosporine dissolved in a solution of about 99% (w/w) 1-perfluorobutyl-pentane and about 1% (w/w) ethanol.

122. A method of reducing the total daily amount of cyclosporine administered topically to a human for the treatment of dry eye disease according to Item 119, wherein said composition consists of the cyclosporine dissolved in a solution of at least about 99% (w/w) 1-perfluorobutyl-pentane and up to about 1% (w/w) ethanol.

123. A method of reducing the total daily amount of cyclosporine administered topically to a human for the treatment of dry eye disease according to Item 119, wherein said composition further comprises up to about 0.5% (w/w) ethanol.

124. A method of reducing the total daily amount of cyclosporine administered topically to a human for the treatment of dry eye disease according to Item 119, wherein said composition consists of the cyclosporine dissolved in a solution of about 99.5% (w/w) 1-perfluorobutyl-pentane and about 0.5% (w/w) ethanol.

125. A method of reducing the total daily amount of cyclosporine administered topically to a human for the treatment of dry eye disease according to Item 119, wherein said composition consists of the cyclosporine dissolved in a solution of at least about 99.5% (w/w) 1-perfluorobutyl-pentane and up to about 0.5% (w/w) ethanol.

126. A method of reducing the total daily amount of cyclosporine administered topically to a human for the treatment of dry eye disease according to any of Items 119 to 125, wherein the single drop of said composition has a drop volume of about 10 μl and the single drop of said emulsion has a drop volume of about 28.5 μl.

127. A method of reducing the total daily amount of cyclosporine administered topically to a human for the treatment of dry eye disease according to any of Items 119 to 125, wherein the systemic exposure to cyclosporine is reduced as compared to twice daily topical administration of a single drop of a 0.05% (w/v) cyclosporine aqueous (o/w) emulsion.

128. A method of reducing the total daily amount of cyclosporine administered topically to a human for the treatment of dry eye disease according to any one of Items 119 to 125, wherein one or more adverse effects are reduced as compared to twice daily topical administration of a single drop of a 0.05% (w/v) cyclosporine aqueous (o/w) emulsion.

129. A method of reducing the total daily amount of cyclosporine administered topically to a human for the treatment of dry eye disease according to any of Items 119 to 125, wherein the adverse effects are selected from the group consisting of visual blurring, eye pain, and eye irritation.

130. A method of reducing the total daily amount of cyclosporine administered topically to a human for the treatment of dry eye disease, the method comprising topically administering twice daily to an eye of a human with dry eye disease a single drop of a composition comprising about 0.1% (w/v) cyclosporine dissolved in 1-perfluorobutyl-pentane, wherein said composition is substantially free of water and is substantially free of a preservative, wherein the amount of cyclosporine administered in a single dose per eye is about 10 μg cyclosporine, and wherein said method reduces the amount of cyclosporine per total daily dose by about 30% and is at least as therapeutically effective in treating dry eye as compared to twice daily topical administration of a single drop per eye of a 0.05% (w/v) cyclosporine aqueous (o/w) emulsion.

131. A method of reducing the total daily amount of cyclosporine administered topically to a human for the treatment of dry eye disease according to Item 130, wherein said composition further comprises up to about 1% (w/w) ethanol.

132. A method of reducing the total daily amount of cyclosporine administered topically to a human for the treatment of dry eye disease according to Item 130, wherein said composition consists of the cyclosporine dissolved in a solution of about 99% (w/w) 1-perfluorobutyl-pentane and about 1% (w/w) ethanol.

133. A method of reducing the total daily amount of cyclosporine administered topically to a human for the treatment of dry eye disease according to Item 130, wherein said composition consists of the cyclosporine dissolved in a solution of at least about 99% (w/w) 1-perfluorobutyl-pentane and up to about 1% (w/w) ethanol.

134. A method of reducing the total daily amount of cyclosporine administered topically to a human for the treatment of dry eye disease according to Item 130, wherein said composition further comprises up to about 0.5% (w/w) ethanol.

135. A method of reducing the total daily amount of cyclosporine administered topically to a human for the treatment of dry eye disease according to Item 130, wherein said composition consists of the cyclosporine dissolved in a solution of about 99.5% (w/w) 1-perfluorobutyl-pentane and about 0.5% (w/w) ethanol.

136. A method of reducing the total daily amount of cyclosporine administered topically to a human for the treatment of dry eye disease according to Item 130, wherein said composition consists of the cyclosporine dissolved in a solution of at least about 99.5% (w/w) 1-perfluorobutyl-pentane and up to about 0.5% (w/w) ethanol.

137. A method of reducing the total daily amount of cyclosporine administered topically to a human for the treatment of dry eye disease according to any one of Items 130 to 136, wherein the single drop of said composition has a drop volume of about 10 µl and the single drop of said emulsion has a drop volume of about 28.5 µl.

138. A method of reducing the total daily amount of cyclosporine administered topically to a human for the treatment of dry eye disease according to any one of Items 130 to 136, wherein the systemic exposure to cyclosporine is reduced as compared to twice daily topical administration of a single drop of a 0.05% (w/v) cyclosporine aqueous (o/w) emulsion.

139. A method of reducing the total daily amount of cyclosporine administered topically to a human for the treatment of dry eye disease according to any one of Items 130 to 136, wherein one or more adverse effects are reduced as compared to twice daily topical administration of a single drop of a 0.05% (w/v) cyclosporine aqueous (o/w) emulsion.

140. A method of reducing the total daily amount of cyclosporine administered topically to a human for the treatment of dry eye disease according to Item 139, wherein the adverse effects are selected from the group consisting of visual blurring, eye pain, and eye irritation.

Further, the present invention comprises the following items 141 to 177 relating to a composition for treating dry eye disease:

141. A composition for treating dry eye disease comprising about 0.05 to 0.1% (w/v) cyclosporine dissolved in 1-perfluorobutyl-pentane, wherein said composition is therapeutically effective in treating dry eye in a human with dry eye disease when topically administered twice daily in a single dose per eye of about 4 to 12 µg cyclosporine.

142. A composition according to Item 141, wherein said composition further comprises up to about 1% (w/w) ethanol.

143. A composition according to Item 141, wherein said composition consists of the cyclosporine dissolved in a solution of about 99% (w/w) 1-perfluorobutyl-pentane and about 1% (w/w) ethanol.

144. A composition according to Item 141, wherein said composition consists of the cyclosporine dissolved in a solution of at least about 99% (w/w) 1-perfluorobutyl-pentane and up to about 1% (w/w) ethanol.

145. A composition according to Item 141, wherein said composition further comprises up to about 0.5% (w/w) ethanol.

146. A composition according to Item 141, wherein said composition consists of the cyclosporine dissolved in a solution of about 99.5% (w/w) 1-perfluorobutyl-pentane and about 0.5% (w/w) ethanol.

147. A composition according to Item 141, wherein said composition consists of the cyclosporine dissolved in a solution of at least about 99.5% (w/w) 1-perfluorobutyl-pentane and up to about 0.5% (w/w) ethanol.

148. A composition according to Item 141, wherein said cyclosporine concentration is about 0.05% (w/v) cyclosporine and said single dose per eye is about 5 µg cyclosporine and wherein said composition is substantially free of water and is substantially free of a preservative.

149. A composition according to Item 148, wherein said composition further comprises up to about 1% (w/w) ethanol.

150. A composition according to Item 148, wherein said composition consists of the cyclosporine dissolved in a solution of about 99% (w/w) 1-perfluorobutyl-pentane and about 1% (w/w) ethanol.

151. A composition according to Item 148, wherein said composition consists of the cyclosporine dissolved in a solution of at least about 99% (w/w) 1-perfluorobutyl-pentane and up to about 1% (w/w) ethanol.

152. A composition according to Item 148, wherein said composition further comprises up to about 0.5% (w/w) ethanol.

153. A composition according to Item 148, wherein said composition consists of the cyclosporine dissolved in about 99.5% (w/w) 1-perfluorobutyl-pentane and about 0.5% (w/w) ethanol.

154. A composition according to Item 148, wherein said composition consists of the cyclosporine dissolved in at least about 99.5% (w/w) 1-perfluorobutyl-pentane and up to about 0.5% (w/w) ethanol.

155. A composition according to any of the items 148 to 154, wherein said composition is effective in reducing corneal staining.

156. A composition according to Item 155, wherein the reduction in corneal staining is achieved over a four month treatment period.

157. A composition according to any of the items 148 to 154, wherein said composition is effective in reducing central corneal staining and/or any one or combination of inferior, superior, nasal, or temporal corneal staining.

158. A composition according to any of the items 148 to 154, wherein said composition is effective in achieving an early onset of action.

159. A composition according to Item 130 or item 158, wherein said early onset of action is measured by reduction in corneal and conjunctival staining and is achieved in about 2 to 4 weeks.

160. A composition according to any of the items 148 to 154, wherein said composition is effective in reducing visual impairment associated with dry eye disease.

161. A composition according to any of the items 148 to 154, wherein said composition is effective in reducing ocular surface damage associated with dry eye.
162. A composition according to any of the items 148 to 154, wherein said composition is safe, well tolerated and comfortable to the eye of the human
163. A composition according to Item 141, wherein said cyclosporine concentration is about 0.10% (w/v) cyclosporine and said single dose per eye is about 10 μg cyclosporine and wherein said composition is substantially free of water and is substantially free of a preservative.
164. A composition according to Item 163, wherein said composition further comprises up to about 1% (w/w) ethanol.
165. A composition according to Item 163, wherein said composition consists of the cyclosporine dissolved in a solution of about 99% (w/w) 1-perfluorobutyl-pentane and about 1% (w/w) ethanol.
166. A composition according to Item 163, wherein said composition consists of the cyclosporine dissolved in a solution of at least about 99% (w/w) 1-perfluorobutyl-pentane and up to about 1% (w/w) ethanol.
167. A composition according to Item 163, wherein said composition further comprises up to about 0.5% (w/w) ethanol.
168. A composition according to Item 163, wherein said composition consists of the cyclosporine dissolved in a solution of about 99.5% (w/w) 1-perfluorobutyl-pentane and about 0.5% (w/w) ethanol.
169. A composition according to Item 163, wherein said composition consists of cyclosporine dissolved in a solution of at least about 99.5% (w/w) 1-perfluorobutyl-pentane and up to about 0.5% (w/w) ethanol.
170. A composition according to any of the items 163 to 169, wherein said composition is effective in reducing corneal staining.
171. A composition according to Item 170, wherein the reduction in corneal staining is achieved over a four month treatment period.
172. A composition according to any of the items 163 to 169, wherein said composition is effective in reducing central corneal staining and/or any one or combination of inferior, superior, nasal, or temporal corneal staining.
173. A composition according to any of the items 163 to 169, wherein said composition is effective in achieving an early onset of action.
174. A composition according to Item 173, wherein said early onset of action is measured by reduction in corneal and conjunctival staining and is achieved in about 2 to 4 weeks.
175. A composition according to any of the items 163 to 169, wherein said composition is effective in reducing visual impairment associated with dry eye disease.
176. A composition according to any of the items 163 to 169, wherein said composition is effective in reducing ocular surface damage associated with dry eye.
177. A composition according to any of the items 163 to 169, wherein said composition is safe, well tolerated and comfortable to the eye of the human.

Further, the present invention comprises the following items 178 to 214, relating to a composition effective in treating dry eye disease in a human with a reduction in total daily amount of cyclosporine:

178. A composition effective in treating dry eye disease in a human with a reduction in total daily amount of cyclosporine administered topically to said human, the composition comprising about 0.05 to 0.1% (w/v) cyclosporine dissolved in 1-perfluorobutyl-pentane, wherein the composition is topically administered twice daily in a single dose per eye of about 4 to 12 μg cyclosporine and wherein the total daily amount of cyclosporine is between about 30 to 65% less than a 0.05% (w/v) cyclosporine aqueous (o/w) emulsion topically administered twice daily in a single drop per eye.
179. A composition according to Item 178, wherein said composition further comprises up to about 1% (w/w) ethanol.
180. A composition according to Item 178, wherein said composition consists of the cyclosporine dissolved in a solution of about 99% (w/w) 1-perfluorobutyl-pentane and about 1% (w/w) ethanol.
181. A composition according to Item 178, wherein said composition consists of the cyclosporine dissolved in a solution of at least about 99% (w/w) 1-perfluorobutyl-pentane and up to about 1% (w/w) ethanol.
182. A composition according to Item 178, wherein said composition further comprises up to about 0.5% (w/w) ethanol.
183. A composition according to Item 178, wherein said composition consists of the cyclosporine dissolved in a solution of about 99.5% (w/w) 1-perfluorobutyl-pentane and about 0.5% (w/w) ethanol.
184. A composition according to Item 178, wherein said composition consists of the cyclosporine dissolved in a solution of at least about 99.5% (w/w) 1-perfluorobutyl-pentane and up to about 0.5% (w/w) ethanol.
185. A composition according to Item 178, wherein said cyclosporine concentration is about 0.05% (w/v) cyclosporine, wherein said composition is substantially free of water and is substantially free of a preservative, wherein said single dose per eye is about 5 μg cyclosporine with a single drop volume of about 10 μl, and wherein the total daily amount of cyclosporine is about 65% less than a 0.05% (w/v) cyclosporine aqueous (o/w) emulsion topically administered twice daily in a single drop per eye having a volume of about 28.5 μl.
186. A composition according to Item 185, wherein said composition further comprises up to about 1% (w/w) ethanol.
187. A composition according to Item 185, wherein said composition consists of the cyclosporine dissolved in a solution of about 99% (w/w) 1-perfluorobutyl-pentane and about 1% (w/w) ethanol.
188. A composition according to Item 185, wherein said composition consists of the cyclosporine dissolved in a solution of at least about 99% (w/w) 1-perfluorobutyl-pentane and up to about 1% (w/w) ethanol.
189. A composition according to Item 185, wherein said composition further comprises up to about 0.5% (w/w) ethanol.
190. A composition according to Item 185, wherein said composition consists of the cyclosporine dissolved in a solution of about 99.5% (w/w) 1-perfluorobutyl-pentane and about 0.5% (w/w) ethanol.
191. A composition according to Item 185, wherein said composition consists of the cyclosporine dissolved in a solution of at least about 99.5% (w/w) 1-perfluorobutyl-pentane and up to about 0.5% (w/w) ethanol.
192. A composition according to any of the items 185 to 191, wherein said composition is effective in reducing corneal staining.

193. A composition according to Item 192, wherein the reduction in corneal staining is achieved over a four month treatment period.
194. A composition according to any of the items 185 to 191, wherein said composition is effective in reducing central corneal staining and/or any one or combination of inferior, superior, nasal, or temporal corneal staining.
195. A composition according to any of the items 185 to 191, wherein said composition is effective in achieving an early onset of action.
196. A composition according to Item 195, wherein said early onset of action is measured by reduction in corneal and conjunctival staining and is achieved in about 2 to 4 weeks.
197. A composition according to any of the items 185 to 191, wherein said composition is effective in reducing visual impairment associated with dry eye disease.
198. A composition according to any of the items 185 to 191, wherein said composition is effective in reducing ocular surface damage associated with dry eye.
199. A composition according to any of the items 183 to 189 or items 185 to 191, wherein said composition is safe, well tolerated and comfortable to the eye of the human
200. A composition according to Item 178, wherein said cyclosporine concentration is about 0.10% (w/v) cyclosporine, wherein said composition is substantially free of water and is substantially free of a preservative, wherein said single dose per eye is about 10 μg cyclosporine with a single drop volume of about 10 μl, and wherein the total daily amount of cyclosporine is about 30% less than a 0.05% (w/v) cyclosporine aqueous (o/w) emulsion topically administered twice daily in a single drop per eye having a volume of about 28.5 μl.
201. A composition according to Item 200, wherein said composition further comprises up to about 1% (w/w) ethanol.
202. A composition according to Item 200, wherein said composition consists of the cyclosporine dissolved in a solution of about 99% (w/w) 1-perfluorobutyl-pentane and about 1% (w/w) ethanol.
203. A composition according to Item 200, wherein said composition consists of the cyclosporine dissolved in a solution of at least about 99% (w/w) 1-perfluorobutyl-pentane and up to about 1% (w/w) ethanol.
204. A composition according to Item 200, wherein said composition further comprises up to about 0.5% (w/w) ethanol.
205. A composition according to Item 200, wherein said composition consists of the cyclosporine dissolved in a solution of about 99.5% (w/w) 1-perfluorobutyl-pentane and about 0.5% (w/w) ethanol.
206. A composition according to Item 200, wherein said composition consists of the cyclosporine dissolved in a solution of at least about 99.5% (w/w) 1-perfluorobutyl-pentane and up to about 0.5% (w/w) ethanol.
207. A composition according to any of the items 200 to 206, wherein said composition is effective in reducing corneal staining.
208. A composition according to Item 207, wherein the reduction in corneal staining is achieved over a four month treatment period.
209. A composition according to any of the items 200 to 206, wherein said composition is effective in reducing central corneal staining and/or any one or combination of inferior, superior, nasal, or temporal corneal staining.
210. A composition according to any of the items 200 to 206, wherein said composition is effective in achieving an early onset of action.
211. A composition according to Item 210, wherein said early onset of action is measured by reduction in corneal and conjunctival staining and is achieved in about 2 to 4 weeks.
212. A composition according to any of the items 200 to 206, wherein said composition is effective in reducing visual impairment associated with dry eye disease.
213. A composition according to any of the items 200 to 206, wherein said composition is effective in reducing ocular surface damage associated with
214. A composition according to any of the items 200 to 206, wherein said composition is safe, well tolerated and comfortable to the eye of the human.

Further, the present invention comprises the following items 215 to 251, relating to a composition for reducing reading impairment associated with dry eye disease:

215. A composition for reducing reading impairment associated with dry eye disease comprising about 0.05 to 0.1% (w/v) cyclosporine dissolved in 1-perfluorobutyl-pentane, wherein said composition is effective in reducing reading impairment in a human with dry eye disease when topically administered twice daily, in a single dose per eye of about 4 to 12 μg cyclosporine.
216. A composition according to Item 215, wherein said composition further comprises up to about 1% (w/w) ethanol.
217. A composition according to Item 215, wherein said composition consists of the cyclosporine dissolved in a solution of about 99% (w/w) 1-perfluorobutyl-pentane and about 1% (w/w) ethanol.
218. A composition according to Item 215, wherein said composition consists of the cyclosporine dissolved in a solution of at least about 99% (w/w) 1-perfluorobutyl-pentane and up to about 1% (w/w) ethanol.
219. A composition according to Item 215, wherein said composition further comprises up to about 0.5% (w/w) ethanol.
220. A composition according to Item 215, wherein said composition consists of the cyclosporine dissolved in a solution of about 99.5% (w/w) 1-perfluorobutyl-pentane and about 0.5% (w/w) ethanol.
221. A composition according to Item 215, wherein said composition consists of the cyclosporine dissolved in a solution of at least about 99.5% (w/w) 1-perfluorobutyl-pentane and up to about 0.5% (w/w) ethanol.
222. A composition according to Item 215, wherein said cyclosporine concentration is about 0.05% (w/v) cyclosporine and said single dose per eye is about 5 μg cyclosporine and wherein said composition is substantially free of water and is substantially free of a preservative.
223. A composition according to Item 222, wherein said composition further comprises up to about 1% (w/w) ethanol.
224. A composition according to Item 222, wherein said composition consists of the cyclosporine dissolved in a solution of about 99% (w/w) 1-perfluorobutyl-pentane and about 1% (w/w) ethanol.
225. A composition according to Item 222, wherein said composition consists of the cyclosporine dissolved in a solution of at least about 99% (w/w) 1-perfluorobutyl-pentane and up to about 1% (w/w) ethanol.

226. A composition according to Item 222, wherein said composition further comprises up to about 0.5% (w/w) ethanol.
227. A composition according to Item 222, wherein said composition consists of cyclosporine dissolved in a solution of about 99.5% (w/w) 1-perfluorobutyl-pentane and about 0.5% (w/w) ethanol.
228. A composition according to Item 222, wherein said composition consists of cyclosporine dissolved in a solution of at least about 99.5% (w/w) 1-perfluorobutyl-pentane and up to about 0.5% (w/w) ethanol.
229. A composition according to any of the items 222 to 228, wherein said composition is effective in reducing corneal staining.
230. A composition according to Item 229, wherein the reduction in corneal staining is achieved over a four month treatment period.
231. A composition according to any of the items 222 to 228, wherein said composition is effective in reducing central corneal staining and/or any one or combination of inferior, superior, nasal, or temporal corneal staining.
232. A composition according to any of the items 222 to 228, wherein said composition is effective in achieving an early onset of action.
233. A composition according to Item 232, wherein said early onset of action is measured by reduction in corneal and conjunctival staining and is achieved in about 2 to 4 weeks.
234. A composition according to any of the items 222 to 228, wherein said composition is effective in reducing visual impairment associated with dry eye disease.
235. A composition according to any of the items 222 to 228, wherein said composition is effective in reducing ocular surface damage associated with dry eye.
236. A composition according to any of the items 222 to 228, wherein said composition is safe, well tolerated and comfortable to the eye of the human
237. A composition according to Item 215, wherein said cyclosporine concentration is about 0.10% (w/v) cyclosporine and said single dose per eye is about 10 μg cyclosporine and wherein said composition is substantially free of water and is substantially free of a preservative.
238. A composition according to Item 237, wherein said composition further comprises up to about 1% (w/w) ethanol.
239. A composition according to Item 237, wherein said composition consists of the cyclosporine dissolved in a solution of about 99% (w/w) 1-perfluorobutyl-pentane and about 1% (w/w) ethanol.
240. A composition according to Item 237, wherein said composition consists of the cyclosporine dissolved in a solution of at least about 99% (w/w) 1-perfluorobutyl-pentane and up to about 1% (w/w) ethanol.
241. A composition according to Item 237, wherein said composition further comprises up to about 0.5% (w/w) ethanol.
242. A composition according to Item 237, wherein said composition consists of the cyclosporine dissolved in a solution of about 99.5% (w/w) 1-perfluorobutyl-pentane and about 0.5% (w/w) ethanol.
243. A composition according to Item 237, wherein said composition consists of the cyclosporine dissolved in a solution of at least about 99.5% (w/w) 1-perfluorobutyl-pentane and up to about 0.5% (w/w) ethanol.
244. A composition according to any of the items 237 to 243, wherein said composition is effective in reducing corneal staining.
245. A composition according to Item 244, wherein the reduction in corneal staining is achieved over a four month treatment period.
246. A composition according to any of the items 237 to 243, wherein said composition is effective in reducing central corneal staining and/or any one or combination of inferior, superior, nasal, or temporal corneal staining.
247. A composition according to any of the items 237 to 243, wherein said composition is effective in achieving an early onset of action.
248. A composition according to Item 247, wherein said early onset of action is measured by reduction in corneal and conjunctival staining and is achieved in about 2 to 4 weeks.
249. A composition according to any of the items 237 to 243, wherein said composition is effective in reducing visual impairment associated with dry eye disease.
250. A composition according to any of the items 237 to 243, wherein said composition is effective in reducing ocular surface damage associated with dry eye.
251. A composition according to any of the items 237 to 243, wherein said composition is safe, well tolerated and comfortable to the eye of the human.

Further, the present invention comprises the following items 252 to 288 relating to a composition for reducing ocular surface damage associated with dry eye disease:

252. A composition for reducing ocular surface damage associated with dry eye disease comprising about 0.05 to 0.1% (w/v) cyclosporine dissolved in 1-perfluorobutyl-pentane, wherein said composition is effective in reducing ocular surface damage in a human with dry eye disease when topically administered twice daily, in a single dose per eye of about 4 to 12 μg cyclosporine.
253. A composition according to Item 252, wherein said composition further comprises up to about 1% (w/w) ethanol.
254. A composition according to Item 252, wherein said composition consists of the cyclosporine dissolved in a solution of about 99% (w/w) 1-perfluorobutyl-pentane and about 1% (w/w) ethanol.
255. A composition according to Item 252, wherein said composition consists of the cyclosporine dissolved in a solution of at least about 99% (w/w) 1-perfluorobutyl-pentane and up to about 1% (w/w) ethanol.
256. A composition according to Item 252, wherein said composition further comprises up to about 0.5% (w/w) ethanol.
257. A composition according to Item 252, wherein said composition consists of the cyclosporine dissolved in a solution of about 99.5% (w/w) 1-perfluorobutyl-pentane and about 0.5% (w/w) ethanol.
258. A composition according to Item 252, wherein said composition consists of the cyclosporine dissolved in a solution of at least about 99.5% (w/w) 1-perfluorobutyl-pentane and up to about 0.5% (w/w) ethanol.
259. A composition according to Item 252, wherein said cyclosporine concentration is about 0.05% (w/v) cyclosporine and said single dose per eye is about 5 μg cyclosporine and wherein said composition is substantially free of water and is substantially free of a preservative.
260. A composition according to Item 259, wherein said composition further comprises up to about 1% (w/w) ethanol.

261. A composition according to Item 259, wherein said composition consists of cyclosporine dissolved in a solution of about 99% (w/w) 1-perfluorobutyl-pentane and about 1% (w/w) ethanol.
262. A composition according to Item 259, wherein said composition consists of the cyclosporine dissolved in a solution of at least about 99% (w/w) 1-perfluorobutyl-pentane and up to about 1% (w/w) ethanol.
263. A composition according to Item 259, wherein said composition further comprises up to about 0.5% (w/w) ethanol.
264. A composition according to Item 259, wherein said composition consists of the cyclosporine dissolved in a solution of about 99.5% (w/w) 1-perfluorobutyl-pentane and about 0.5% (w/w) ethanol.
265. A composition according to Item 259, wherein said composition consists of the cyclosporine dissolved in a solution of at least about 99.5% (w/w) 1-perfluorobutyl-pentane and up to about 0.5% (w/w) ethanol.
266. A composition according to any of the items 259 to 265, wherein said composition is effective in reducing corneal staining.
267. A composition according to Item 266, wherein the reduction in corneal staining is achieved over a four month treatment period.
268. A composition according to any of the items 259 to 265, wherein said composition is effective in reducing central corneal staining and/or any one or combination of inferior, superior, nasal, or temporal corneal staining.
269. A composition according to any of the items 259 to 265, wherein said composition is effective in achieving an early onset of action.
270. A composition according to Item 269, wherein said early onset of action is measured by reduction in corneal and conjunctival staining and is achieved in about 2 to 4 weeks.
271. A composition according to any of the items 259 to 265, wherein said composition is effective in reducing visual impairment associated with dry eye disease.
272. A composition according to any of the items 259 to 265, wherein said composition is effective in reducing ocular surface damage associated with
273. A composition according to any of the items 259 to 265, wherein said composition is safe, well tolerated and comfortable to the eye of the human.
274. A composition according to Item 252, wherein said cyclosporine concentration is about 0.10% (w/v) cyclosporine and said single dose per eye is about 10 μg cyclosporine and wherein said composition is substantially free of water and is substantially free of a preservative.
275. A composition according to Item 274, wherein said composition further comprises up to about 1% (w/w) ethanol.
276. A composition according to Item 274, wherein said composition consists of the cyclosporine dissolved in a solution of about 99% (w/w) 1-perfluorobutyl-pentane and about 1% (w/w) ethanol.
277. A composition according to Item 274, wherein said composition consists of the cyclosporine dissolved in a solution of at least about 99% (w/w) 1-perfluorobutyl-pentane and up to about 1% (w/w) ethanol.
278. A composition according to Item 274, wherein said composition further comprises up to about 0.5% (w/w) ethanol.
279. A composition according to Item 274, wherein said composition consists of the cyclosporine dissolved in a solution of about 99.5% (w/w) 1-perfluorobutyl-pentane and about 0.5% (w/w) ethanol.
280. A composition according to Item 274, wherein said composition consists of the cyclosporine dissolved in a solution of at least about 99.5% (w/w) 1-perfluorobutyl-pentane and up to about 0.5% (w/w) ethanol.
281. A composition according to any of the items 274 to 280, wherein said composition is effective in reducing corneal staining.
282. A composition according to Item 281, wherein the reduction in corneal staining is achieved over a four month treatment period.
283. A composition according to any of the items 274 to 280, wherein said composition is effective in reducing central corneal staining and/or any one or combination of inferior, superior, nasal, or temporal corneal staining.
284. A composition according to any of the items 274 to 280, wherein said composition is effective in achieving an early onset of action.
285. A composition according to Item 284, wherein said early onset of action is measured by reduction in corneal and conjunctival staining and is achieved in about 2 to 4 weeks.
286. A composition according to any of the items 274 to 280, wherein said composition is effective in reducing visual impairment associated with dry eye disease.
287. A composition according to any of the items 274 to 280, wherein said composition is effective in reducing ocular surface damage associated with dry eye.
288. A composition according to any of the items 274 to 280, wherein said composition is safe, well tolerated and comfortable to the eye of the human.

The invention further also comprises the following items 289 to 303, relating to:

289. A pharmaceutical composition for use in the topical treatment of dry eye disease, wherein the composition comprises about 0.05 to 0.1% (w/v) cyclosporine dissolved in 1-perfluorobutyl-pentane and wherein the amount of cyclosporine administered in a single dose per eye is about 4 to 12 μg.
290. A pharmaceutical composition for use in the treatment of ocular surface damage in a subject suffering from dry eye disease, wherein the composition comprises about 0.05 to 0.1% (w/v) cyclosporine dissolved in 1-perfluorobutyl-pentane and wherein the amount of cyclosporine administered in a single dose per eye is about 4 to 12 μg.
291. A pharmaceutical composition for use in the treatment of reading impairment in a subject suffering from dry eye disease, wherein the composition comprises about 0.05 to 0.1% (w/v) cyclosporine dissolved in 1-perfluorobutyl-pentane.
292. The pharmaceutical composition for use according to item 291, wherein the amount of cyclosporine administered in a single dose per eye is about 4 to 12 μg.
293. The pharmaceutical composition for use according to any one of the preceding items 289-292, wherein the total daily administered dose per eye is less than about 28 μg.
294. The pharmaceutical composition for use according to any one of the preceding items 289-293, wherein the amount of cyclosporine administered in a single dose per eye is about 5 μg or about 10 μg.
295. The pharmaceutical composition for use according to any one of the preceding items 289-294, wherein the dose of the composition is administered as one single drop to an eye of a subject.

296. The pharmaceutical composition for use according to any one of the preceding items 289-295, wherein the dry eye disease is moderate to severe dry eye disease, and optionally wherein the subject is not responsive to treatment with artificial tears.
297. The pharmaceutical composition for use according to any one of the preceding items 289-296, wherein the composition comprises up to about 1.0% (w/w) ethanol.
298. The pharmaceutical composition for use according to any one of the preceding items 289-297, wherein the composition consists essentially of about 0.05% or 0.1% (w/v) cyclosporine dissolved in 1-perfluorobutyl-pentane, and optionally about 1.0% (w/w) of ethanol.
299. The pharmaceutical composition for use according to any one of the preceding items 289-298, wherein the composition is administered twice per day.
300. A kit comprising a pharmaceutical composition for use according to any one of items 289 to 299, wherein the kit comprises a container for holding the pharmaceutical composition and a drop dispenser adapted for administering about 8 to 12 µl volume of the composition per drop.
301. The kit according to item 300, wherein the container and/or drop dispenser is manufactured from a thermoplastic material, preferably selected from polyethylene or polypropylene.
302. The kit according to item 301, wherein the container is manufactured from polypropylene and wherein the drop dispenser is manufactured from a polyethylene selected from low or high density polyethylene.
303. The kit according to any one of items 300-302, wherein the ratio of the volume of the pharmaceutical composition in the container to the total volume of the container is between 0.4 to 0.7, or wherein the ratio of the volume of the head space of the container to the volume of the pharmaceutical composition is between 0.5 to 1.5.

DESCRIPTION OF THE DRAWINGS

In FIG. 4, the relative reading impairment (expressed as a percentage %) observed in patients treated with CyclASol 0.05% and CyclASol 0.1% versus Baseline (V1, day 1) is compared to the vehicle over visits V2 (2-week follow-up), V3 (4-week follow-up), V4 (12-week follow-up) and V5 (16-week follow-up). Negative relative values indicate an improvement of reading impairment. The comparison demonstrates that reading capability in patients treated with CyclASol 0.05% and CyclASol 0.1% was improved, compared to vehicle at visit V5 (16-week follow-up), resulting in a reduction in reading impairment of 28% and 31% respectively.

Figure 1:
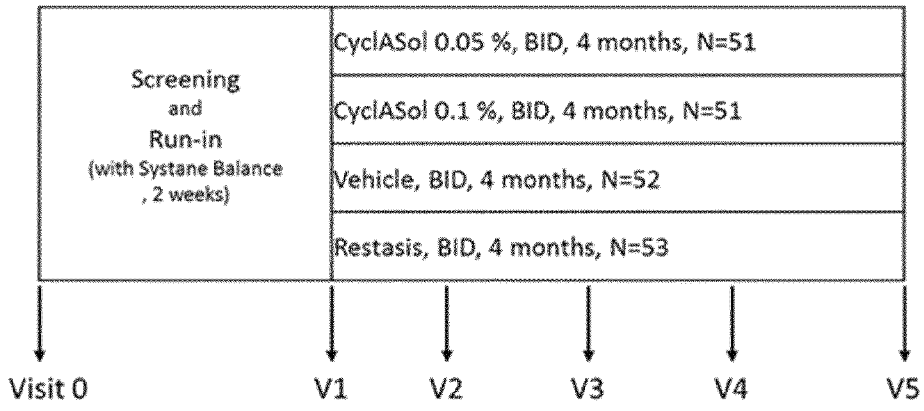
FIG. 1 depicts the study schedule including the screening and a 2-week run-in phase (subjects were provided with lubricant eye drops), followed by a 4-month treatment phase.

The following examples serve to illustrate the invention, however should not to be understood as restricting the scope of the invention.

EXAMPLES

Example 1

Study Setup A Phase 2, multi-center, randomized, double-masked, placebo (vehicle)-controlled clinical study with an open label comparator arm to assess the efficacy, safety and tolerability of topical CyclASol for treatment of dry eye disease was conducted. This dose finding trial in moderate to severe dry eye patients not responding to artificial tears was set up as a 4-arm randomized parallel double masked vehicle controlled study with 2 doses of CyclASol (0.05% and 0.1%) and an open label comparator arm.

CyclASol is a clear ophthalmic solution of Cyclosporine A dissolved in 1-perfluorobutyl-pentane. 1-perfluorobutyl-pentane, which is commonly abbreviated F4H5 is used as the vehicle. The only other component in the formulation is ethanol (1.0% (w/w) as co-solvent.

In addition to the masked vehicle control arm, an open-label treatment arm consisting of Restasis® was included to allow a head to head comparison of effects of CyclASol and Restasis®. Restasis® is an approved medication for dry eye disease, comprising 0.05% Cyclosporine A, formulated as an aqueous emulsion.

Study Plan

| Study Arm | Medication | # Subjects | Dosage |
|---|---|---|---|
| 1 | CyclASol 0.05% | N = 51 | one drop |
| 2 | CyclASol 0.1% | N = 51 | per eye, |
| 3 | Vehicle | N = 52 | twice daily |
| 4 | Restasis 0.05% (open label comparator) | N = 53 | (BID), for 4 months |

CyclASol 0.05%=0.05% (w/v) cyclosporine A, dissolved in 1-perfluorobutylpentane (F4H5) and 1% (w/w) ethanol CyclASol 0.1%=0.1% (w/v) cyclosporine A, dissolved in 1-perfluorobutylpentane (F4H5) and 1% (w/w) ethanol Vehicle=solution of 1-perfluorobutylpentane (F4H5) and 1% (w/w) ethanol Study Population In total of 207 (153 female, 54 male) patients with a subject-reported history of dry eye in both eyes and meeting all other study eligibility criteria were included, with a similar distribution of age and sex across the groups. The subjects were randomized to receive treatment with 0.05% CyclASol, 0.1% CyclASol, Vehicle, or Restasis® in a 1:1:1:1 ratio. The study consisted of two periods: a 14-day run-in period and a 112-day treatment period.

Patients included in the study had to fulfill following criteria:

(a) Be at least 18 years of age;
(b) Provide written informed consent;
(c) Have a subject reported history of dry eye disease in both eyes for at least 6 months prior to Visit 0;
(d) Current use (within 30 days prior to Visit 0) of over-the-counter and/or prescription eye drops for dry eye symptoms at Visit 0;
(e) Have a score of ≥40 on the dryness visual analogue scale at Visit 0 and Visit 1;
(f) Have a total corneal fluorescein staining score of ≥6 (e.g. sum of inferior, superior, central, nasal, and temporal) according to the NEI grading at Visits 0 and Visit 1;
(g) Have a total lissamine green conjunctival score (sum of temporal and nasal) of ≥2, based on the Oxford grading at Visits 0 and Visit 1;
(h) Have a Schirmer's Test I score between ≥2 mm and ≤8 mm at Visits 0 and Visit 1;
(i) Have at least one eye (the same eye) satisfy all criteria for (f), (g), and (h) above;
(j) Be able and willing to follow instructions, including participation in all study assessments and visits.

The patients were examined during the 112-day treatment period according to the following schedule:

| Visit | Day | Purpose |
|---|---|---|
| V0 | Day −14 ± 2 | Screening |
| V1 | Day 1 | Baseline/Randomization |
| V2 | Day 15 ± 1 | 2-week follow-up |
| V3 | Day 29 ± 2 | 4-week follow-up |
| V4 | Day 85 ± 3 | 12-week follow-up |
| V5 | Day 113 ± 3 | 16-week follow-up/Study |

Instructions for Use

The study subjects were instructed to instill one dose (one single droplet) in each eye two times daily (in the morning and in the evening before bed).

The application volume per single dose (10 μL) of CyclASol 0.05%, CyclASol 0.1% solution and vehicle and as well as the amount of active ingredient was significantly lower as compared to the administered single dose of Restasis® 0.05% aqueous (o/w) emulsion (28.5 μL, ref. Restasis NDA 21-023, Clinical Pharmacology Biopharmaceutics Review (s)).

| | CyclASol, 0.05% | CyclASol, 0.1% | Restasis ® 0.05% |
|---|---|---|---|
| Drop volume (1 droplet) | 10 μl | 10 μl | 28.5 μl |
| Single dose, per eye | 5 μg | 10 μg | 14.25 μg |
| Daily dose (2 × per day), per eye | 10 μg | 20 μg | 28.5 μg |
| Dose relative to Restasis ® | 35.1% | 70.2% | 100.0% |
| Total reduction in daily dose exposure | 64.9% | 29.8% | 0.0% |

Study Analysis

At each visit during the 112-day treatment period, each subject was assessed in terms of treatment efficacy using tests including corneal fluorescein staining (NEI Grading); conjunctival staining (Lissamine, Oxford grading) as well as subject symptom assessment questionnaires such as Ocular Surface Disease Index (OSDI, ref. Schiffman R. M. et al 2000; 118:615-621.) questionnaire (including question 6 relating to reading impairment) and dryness severity visual analogue scale (VAS).

For corneal staining (Sook Chun Y et al., Am J Ophthalmol. 2014 May; 157(5):1097-102), 5 μl of 2% preservative-free sodium fluorescein solution was instilled into the inferior conjunctival cul-de-sac of each eye. In order to achieve maximum fluorescence, the fluorescein staining is evaluated only after approximately 3-5 minutes after instillation. A Wratten #12 yellow filter was used to enhance the ability to grade fluorescein staining.

Figure 2:
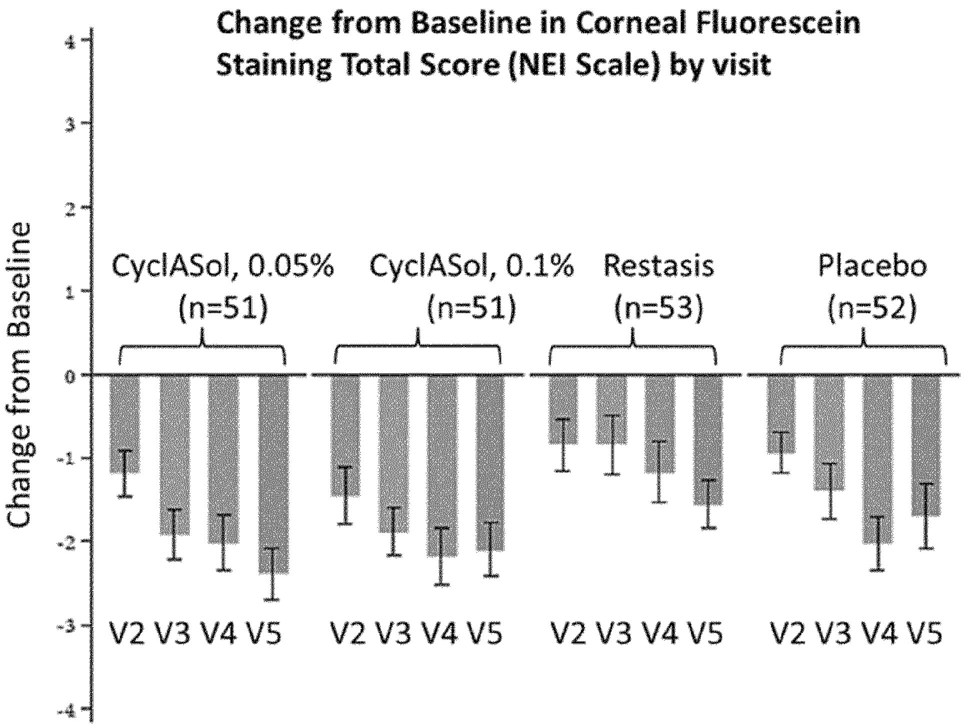
FIG. 2 demonstrates Corneal Fluorescein Staining (the National Eye Institute (NEI) Scale) of patients suffering from moderate to severe dry eye disease treated with a) a 0.05% (w/v) cyclosporine solution in 1-perfluorobutyl-pentane and 1.0% (w/v) ethanol (CyclASol 0.05%); b) a 0.1% (w/v) cyclosporine solution in 1-perfluorobutyl-pentane and 1.0% (w/v) ethanol (CyclASol 0.1%); c) Restasis® (comprising 0.05% (w/v) cyclosporine) and d) the vehicle (1-perfluorobutyl-pentane and 1.0% (w/w) ethanol) alone. Depicted is the change over time of the Corneal Fluorescein Staining Total Score (NEI Scale) as compared to baseline scores obtained prior to commencement of treatment (V1, day 1) for visits V2 (2-week follow-up), V3 (4-week follow-up), V4 (12-week follow-up) and V5 (16-week follow-up). It is observed herein that both CyclASol 0.05% and CyclASol 0.1% provide an earlier onset of effect as well as a higher efficacy when compared to the open label comparator Restasis®. This is surprising since lower volumes (10 µl) were administered to the patients as compared to Restasis® (28.5 µl), which translates to a 30 to 65% reduction of daily exposure of cyclosporine A but at the same time resulting even higher efficacy.
Figure 3:
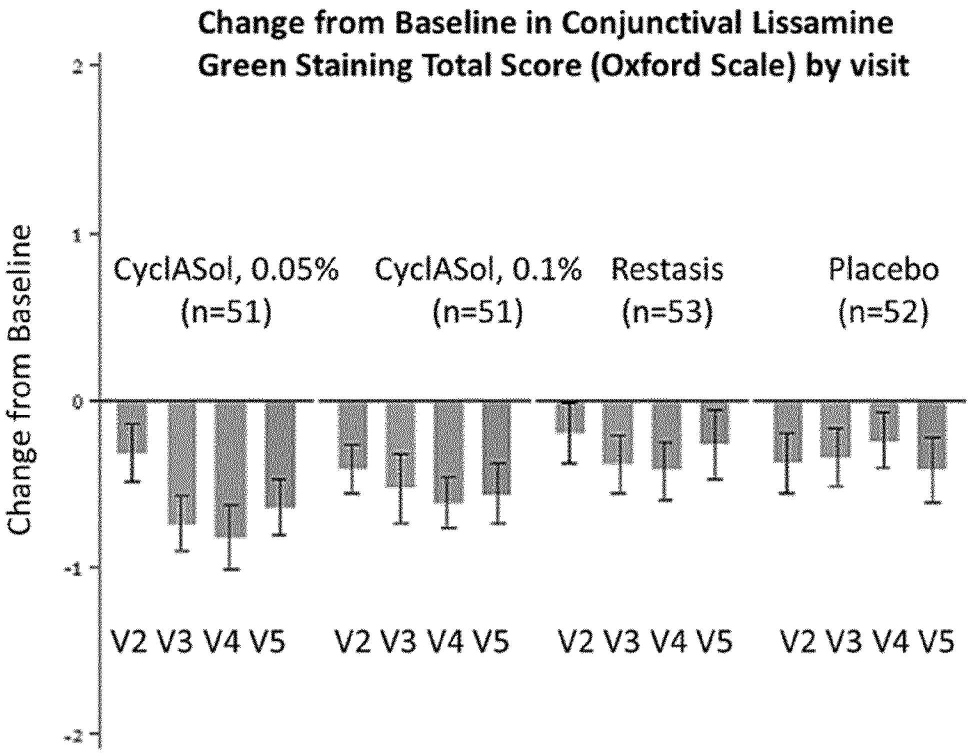
FIG. 3 features results based on Conjunctival Lissamine Green Staining (Oxford Scale) following treatment of patients suffering from moderate to severe dry eye disease with CyclASol 0.05%, CyclASol 0.1%, Restasis® and the vehicle. Depicted is the change of the Conjunctival Lissamine Green Staining Total Score (Oxford Scale) as compared to baseline (V1, day 1) for visits V2 (2-week follow-up), V3 (4-week follow-up), V4 (12-week follow-up) and V5 (16-week follow-up). It is observed that both CyclASol 0.05% and CyclASol 0.1% show an earlier onset of effect as well as higher efficacy when compared to the open label comparator Restasis®. This is surprising since lower volumes (10 µl) are administered to the patients as compared to Restasis® (28.5 µl), which translates to a 30-65% reduction of daily exposure of cyclosporine A to the patients resulting in even higher efficacy.
Figure 4:
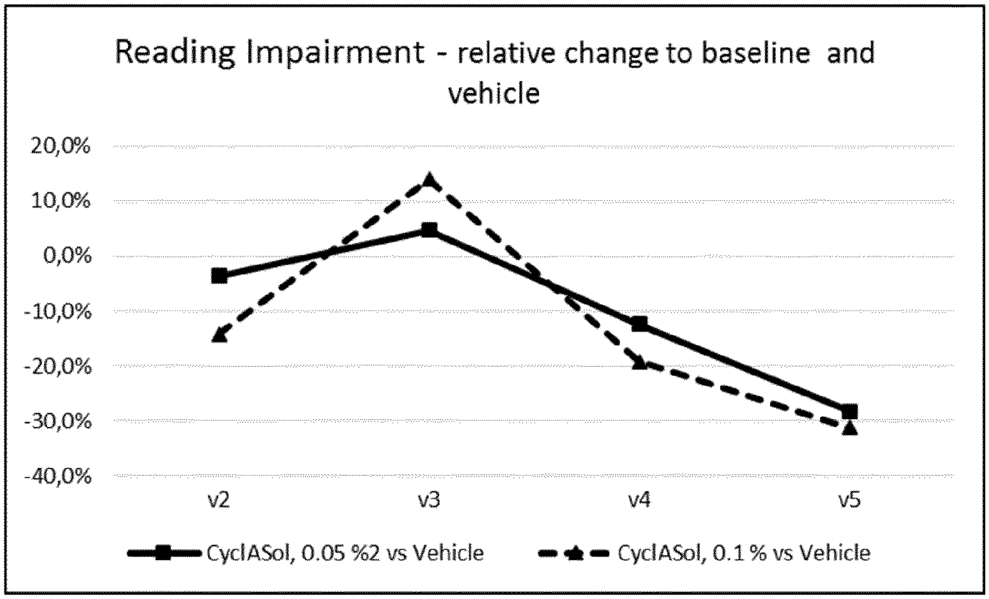
FIG. 4 demonstrates the effect on the treatment of reading impairment of patients suffering from moderate to severe dry eye disease by administration of CyclASol 0.05% and CyclASol 0.1% based on data derived from assessment of the reading assessment portion of the OSDI questionnaire (OSDI, Ocular Surface Disease Index) which relates to a scale of 0 to 4 (with 0 indicating no reading problems and 4 translating to most severe reading problems).
Figure 5:
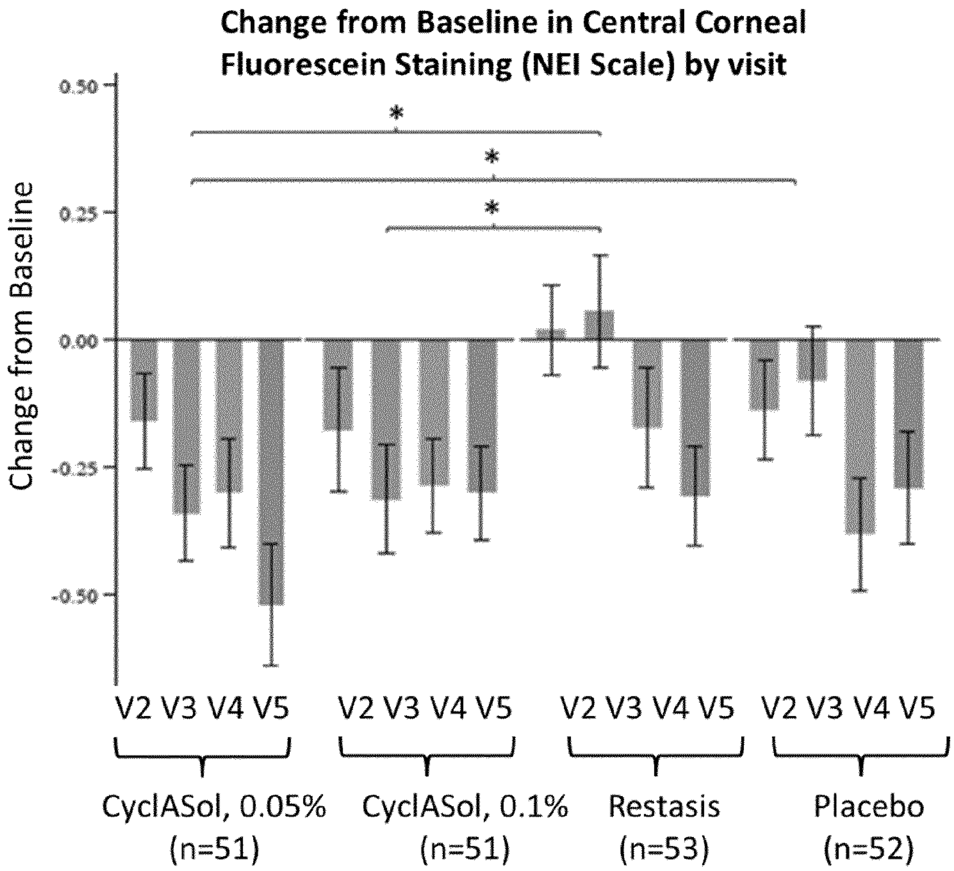
FIG. 5 demonstrates Central Corneal Fluorescein Staining (the National Eye Institute (NEI) Scale) of patients suffering from moderate to severe dry eye disease treated with a) a 0.05% (w/v) cyclosporine solution in 1-perfluorobutyl-pentane and 1.0% (w/v) ethanol (CyclASol 0.05%); b) a 0.1% (w/v) cyclosporine solution in 1-perfluorobutyl-pentane and 1.0% (w/v) ethanol (CyclASol 0.1%); c) Restasis® (comprising 0.05% (w/v) cyclosporine) and d) the vehicle (1-perfluorobutyl-pentane and 1.0% (w/w) ethanol) alone. Depicted is the change over time of the Central Corneal Fluorescein Staining Score (NEI Scale) as compared to baseline scores obtained prior to commencement of treatment (V1, day 1) for visits V2 (2-week follow-up), V3 (4-week follow-up), V4 (12-week follow-up) and V5 (16-week follow-up). It is observed herein that both CyclASol 0.05% and CyclASol 0.1% provide an earlier onset of effect as well as a higher efficacy when compared to the open label comparator Restasis®. This is surprising since lower volumes (10 µl) were administered to the patients as compared to Restasis® (28.5 µl), which translates to a 30 to 65% reduction of daily exposure of cyclosporine A but at the same time resulting even higher efficacy.

The staining was graded with the NEI Grading Scale (The National Eye Institute grading system), with only the cornea being graded. Corneal fluorescein staining scores were obtained for each of the inferior, superior central, temporal, and nasal regions of the cornea based on a 0-3 scale, where a score of 0 means no staining is observed. The term "total corneal fluorescein staining total score" (ref. FIG. 2) refers to a sum of scores from the inferior, superior, central, temporal, and nasal regions of the cornea.

Conjunctival Lissamine Green Staining (Bron A. J. et al, Cornea. 2003; 22:640-650) was conducted by instillation of 10 μl of lissamine green solution into the inferior conjunctival cul-de-sac of a subject. After waiting for approximately 30 seconds the staining was evaluated. The subject was instructed to blink several times to distribute the lissamine green. The staining was graded with the Oxford Grading Scale. Herein, the lissamine staining is represented by punctate dots on a series of panels (A-E). Staining ranges from 0-5 for each panel and 0-10 for the total exposed inter-palpebral conjunctiva. Both nasal and temporal regions were graded separately. A score of 0 meaning no staining. Total conjunctival lissamine green staining scores were obtained, referring to the sum of scores from both temporal and nasal regions of the conjunctiva.

The invention claimed is:

1. A method for treating dry eye disease, the method comprising the step of topically administering to a human patient in need thereof an ophthalmic composition consisting of cyclosporine, 1-perfluorobutylpentane, 2-perfluorobutylpentane, and ethanol; wherein the cyclosporine is present in an amount of 0.1% (w/v), the 1-perfluorobutylpentane is present in an amount of at least 97% (w/w), the 2-perfluorobutylpentane is present in an amount of up to 2% (w/w), and the ethanol is present in an amount of up to 1.0% (w/w); wherein the composition is administered twice per day per eye as a single drop having a volume of 10 µl.

2. The method according to claim 1, wherein the composition comprises up to 1% (w/w) of 2-perfluorobutylpentane.

3. The method according to claim 1, wherein the composition comprises up to 0.5% (w/w) of 2-perfluorobutylpentane.

4. The method according to claim 1, wherein the dry eye disease is moderate to severe dry eye disease.

5. The method according to claim 1, wherein the patient is not responsive to treatment with artificial tears.

6. The method according to claim 4, wherein the moderate to severe dry eye disease is characterized by at least one or a combination of the following selected from the group consisting of:

i) a total corneal fluorescein staining score of >6;

ii) being symptomatic with a score of >40 on the dryness visual analogue scale (VAS);

iii) a score of >20 on the Ocular Surface Disease Index (OSDI); and iv) a Schirmer's Test I score of >2 mm and <8 mm.

7. The method according to claim 1, wherein the patient has at least one eye with a score selected from the group consisting of:

i) a score of >40 on the dryness visual analogue scale (VAS);

ii) a total corneal fluorescein staining score of >6;

iii) a total lissamine green conjunctival staining score of >2; and iv) a Schirmer's Test I score of >2 mm and <8 mm.

8. The method according to claim 1, wherein the patient experiences symptoms selected from the group consisting of blurring, pain, irritation, and or corneal surface damage.

9. The method according to claim 1, wherein the amount of cyclosporine administered in a single dose per eye is 10 µg.

10. The method according to claim 1, wherein the total daily dosage of cyclosporine administered per eye is 20 µg.

11. The method according to claim 1, wherein a reduction in corneal or conjunctival staining is achieved within 2 to 4 weeks.

12. The method according to claim 1, wherein the patient experiences signs of dry eye disease selected from the group consisting of tear hyperosmolarity, tear film instability, and abnormalities in the lipid composition of the tear film.

13. The method according to claim 1, wherein the dry eye disease is aqueous deficient dry eye disease.

14. The method according to claim 1, wherein the dry eye disease is evaporative dry eye disease.

15. The method according to claim 1, wherein the dry eye disease is caused by or associated with Meibomian gland dysfunction.

16. The method according to claim 1, wherein the dry eye disease is caused by or associated with ocular surface disorder.

17. The method according to claim 1, wherein the patient has at least one eye with a Schirmer's Test I score of >2 mm and <8 mm.

18. The method according to claim 1, wherein the patient has at least one eye with a total corneal fluorescein staining score of at least 6.

19. The method according to claim 1, wherein the patient has at least one eye with a total lissamine green conjunctival staining score of at least 2.

20. The method according to claim 1, wherein the patient has suppressed tear production.

21. The method according to claim 1, wherein the patient suffers from reading impairment, and wherein the reading impairment is selected from the group consisting of reading impairment caused by increased ocular discomfort during the task of reading, reading impairment caused by increased ocular discomfort consequent to the task of reading, and reading impairment caused by difficulty in visualizing or perceiving characters while reading.

22. The method according to claim 1, wherein the method provides the patient with a reduction in corneal fluorescein staining.

23. The method according to claim 1, wherein the method provides the patient with a reduction in corneal inflammation.

24. The method according to claim 1, wherein the patient has at least one eye with a central corneal fluorescein staining score of at least 1.

25. The method according to claim 1, wherein the method provides the patient with a reduction in conjunctival lissamine green staining.

26. The method according to claim 1, wherein the method provides the patient with a reduction in conjunctival inflammation.

* * * * *